United States Patent [19]

Kamitani et al.

[11] Patent Number: 5,429,820

[45] Date of Patent: Jul. 4, 1995

[54] COSMETIC COMPOSITION

[75] Inventors: Hiroshi Kamitani, Wakayama; Katsumi Kita, Izumisano; Yoshiaki Fujikura, Utsunomiya; Ryuuji Ochiai, Urayasu; Kazuyuki Yahagi, Tokyo, all of Japan

[73] Assignee: KAO Corporation, Tokyo, Japan

[21] Appl. No.: 865,179

[22] Filed: Apr. 8, 1992

[30] Foreign Application Priority Data

Apr. 8, 1991 [JP] Japan ................... 3-075272
Jul. 24, 1991 [JP] Japan ................... 3-184726
Nov. 7, 1991 [JP] Japan ................... 3-291707

[51] Int. Cl.⁶ .................................... A61K 7/42
[52] U.S. Cl. ........................... 424/401; 424/63; 424/64; 424/70.28; 424/70.3 L
[58] Field of Search ............... 424/401, 64, 70.28, 424/70.3 L, 63; 252/312; 514/938, 941

[56] References Cited

U.S. PATENT DOCUMENTS 3,996,134 12/1976 Osborn et al. ................ 252/312
4,115,314 9/1978 Oppenländer et al. ........ 252/312
4,543,258 9/1985 Urata et al. ................... 514/938

(List continued on next page.)

FOREIGN PATENT DOCUMENTS 663846  5/1965  Belgium .
0168574 1/1986  European Pat. Off. .
0217105 4/1987  European Pat. Off. .
0242792 10/1987 European Pat. Off. .
0277335 8/1988  European Pat. Off. .
0353735 2/1990  European Pat. Off. .
0411202 2/1991  European Pat. Off. .
0487262 5/1992  European Pat. Off. .
2281744 3/1976  France .
2315991 1/1977  France .
2540104 8/1984  France .

(List continued on next page.)

OTHER PUBLICATIONS

Patent Abstracts of Japan, vol. 012, No. 059, (C-478), Feb. 23, 1988, JP-A-62 205 188, Sep. 9, 1987.
Patent Abstracts of Japan, vol. 012, No. 059, (C-478), Feb. 23, 1988, JP-A-62 205, 187, Sep. 9, 1987.
Patent Abstracts of Japan, vol. 14, No. 412, (C-0755), Sep. 6, 1990, JP-21 57 035, Jun. 15, 1990.
Journal of Cell Biology, vol. 12, 1962, pp. 207-219, V.

(List continued on next page.)

Primary Examiner—Thurman K. Page
Assistant Examiner—Neil Levy
Attorney, Agent, or Firm—Oblon, Spivak, McClelland, Maier & Neustadt

[57] ABSTRACT

A cosmetic composition comprises:
(A) a nonionic amphipathic compound having in the molecule thereof at least one branched alkyl or alkenyl group having 10–36 carbon atoms and at least three hydroxyl groups, and having a lamellar liquid crystal structure itself at 25° C. and at 50° C. or higher; and
(B) a compound represented by formula (1):

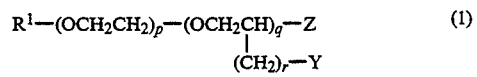

wherein $R^1$ is a hydrogen atom, a lower alkyl group or a group

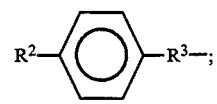

$R^2$ is a hydrogen atom, a methyl group or a methoxy group; $R^3$ is a direct bond or a saturated or unsaturated divalent hydrocarbon group having 1 to 3 carbon atoms; each Y and each Z are independently hydrogen atoms or hydroxyl groups; and p, q and r are each independently integers of 0 to 5, excepting the case where all of p, q and r are zero and Z is H, and the case where all of p, q and r are zero, $R^1$ is H and Z is OH.

14 Claims, 4 Drawing Sheets

U.S. PATENT DOCUMENTS

| | | | |
|---|---|---|---|
| 4,767,625 | 8/1988 | Mitsuno et al. | 424/401 |
| 4,940,574 | 7/1990 | Kaplan | 424/59 |
| 5,041,283 | 8/1991 | Kita et al. | 424/64 |

FOREIGN PATENT DOCUMENTS

| | | |
|---|---|---|
| 2045650 | 4/1971 | Germany . |
| 3144371 | 6/1982 | Germany . |
| 385050 | 9/1960 | Japan . |
| 52-6375 | 1/1977 | Japan . |
| 61-267505 | 11/1986 | Japan . |
| 61-56016 | 12/1986 | Japan . |
| 62-96585 | 5/1987 | Japan . |
| 63-23737 | 2/1988 | Japan . |
| 63-258804 | 10/1988 | Japan . |
| 2130206 | 5/1984 | United Kingdom . |
| 2155472 | 9/1985 | United Kingdom . |
| WO86/02635 | 5/1986 | WIPO . |

OTHER PUBLICATIONS

Luzzati, et al., "The Structure of the Liquid–Crystalline Phases of Lipid–Water Systems".

Surface, vol. 11, No. 10, 1973, pp. 579–590, S. Kuroiwa, "Structures and Properties of Liquid Crystals Formed in the Highly Concentrated Aqueous Solutions of Surfactants".

JAOCS, vol. 51, Dec. 1974, pp. 522–527, D. H. McMahon, et al., "Characterization of Products From Clay Catalyzed Polymerization of Tall Oil Fatty Acids[1]".

Patent Abstracts of Japan, vol. 014, No. 246, (C–0722) 25 May 1990 & JP2064198 (KAO Corp.) 5 Mar. 1990, 2 pages.

Derwent Abstract JP2064198 A 900305 DW9015, 1 page.

Agric. Biol. Chem. vol. 46, No. 1, 1982, pp. 263–268 Ogawa T. et al. 'Synthesis of Glycoglycerolipids: 3-0-Mannooligosyl-1, 2-di-O-tetradexyl-sn-Glycerol'.

Agric. Biol. Chem. vol. 55, No. 8, 1991, pp. 2083–2089 Nakano H. et al. 'Esterification of glycosides with Glycerol and trimethylolpropane moieties by Candida cylidracea Lipase'.

Agric. Biol. Chem. vol. 46, No. 1, 1982, pp. 255–262 Ogawa et al. "Synthesis of 3-0-Glycosy-1, 2-di-0-tetradecyl-sn-Glycerol".

Derwent Abstract JP55160710 A 801214 DW8109, 1 page.

Patent Abstracts of Japan, vol. 5, No. 128, (C–67)(800) 18 Aug., 1981 & JP-A-56 062 536 (Nippon Saafuakutanto Kogyo KK) 28 May 1981, 1 page.

Patent Abstracts of Japan, JP56062536 A 810528 DW8129, 1 page.

Chemical Abstracts, vol. 90, No. 22, May 1979, Columbus, Ohio, US; abstract No. 174523w, Suga S. et al. 'maltitol esters for cosmetics' p. 382.

Chemical Abstracts, vol. 86, No. 6, Feb. 1977, Columbus, Ohio, US; abstract No. 34151r, 'Cosmetics containing esters of glycerol or sorbitol condensation products' p. 287; col. 34156 'maltitol esters for cosmetics' p. 382.

Derwent Abstract JP4089450 A 920323 DW9218. 1 page.

Patent Abstracts of Japan, vol. 106, No. 315, (C–961) 10 Jul. 1990, & JP-A-04 089 450 (KAO Corp.) 23 Mar. 1992, 1 page.

Derwent Abstract JP1172311 A 890707 DW8933, 1 page.

Derwent Abstract JP63126820 A 880530 DW8827, 1 page.

COSMETIC COMPOSITION

BACKGROUND OF THE INVENTION

1. Field of the Invention

This invention relates to a cosmetic composition, and more particularly to a cosmetic composition which provides excellent moisturizing effect and excellent extendibility when applied to the skin, hair and the like, and exhibits excellent smoothness under dry and wet conditions and has excellent emulsion stability. This invention also relates to a polyol glyceryl ether which is usable as an ingredient of the above cosmetic composition.

2. Description of the Background Art

Although various moisturizers are generally incorporated in cosmetic compositions, conventional moisturizers have a problem in that they cannot provide sufficient moisturizing effects when incorporated in small amounts, and that when a large amount of moisturizer is incorporated into a cosmetic composition to sufficiently provide the moisturizing effect, the stability of the system is deteriorated.

Emulsion-type cosmetic compositions are widely used, because they can give a proper amount of oil and water to the skin and hair. Various types of emulsions which present different physical properties and give different feels to users are obtainable by changing the kind and amount of the oil.

However, since emulsions are unstable systems in terms of their thermodynamics, the stabilization of emulsions is difficult. Therefore, many studies and experiments have been carried out to solve this problem. One proposed measure is the addition of an emulsification aid having surface activity. Examples of the emulsification aid include cationic surfactants, anionic surfactants, amphoteric surfactants and nonionic surfactants, among which nonionic surfactants are the most preferred, because various oils can be used with them and they are applicable to various cosmetic compositions.

Known as a nonionic emulsification aid is a liquid-crystal-forming compound such as a higher alcohol and long chain branched alkyltriol (Japanese patent publication No. 38-5050, Japanese patent application laid-open No. 63258804); a long chain alkyl polyglyceryl ether (Japanese patent application laid-open Nos. 52-6375 and 63-23737); an ethylene oxide adduct of higher alcohol (Japanese patent application laid-open No. 62-96585); and a higher fatty acid polyol ester (Japanese patent publication No. 61-56016). These compounds, however, do not form lamellar liquid crystals when used singly, giving an oily feel to users when applied to the skin or hair. Although they form lamellar liquid crystals when combined with other ingredients, the temperature range within which lamellar liquid crystals are formed is narrow. These compounds therefore have a problem in that they cannot keep cosmetic compositions stable.

Another problem in the preparation of cosmetic compositions is explained: many active ingredients in cosmetic compositions have high melting points and they are in crystal and/or solid form at normal temperature. When they are not uniformly emulsified or dispersed in the cosmetic composition and exist as solids and/or crystals, the effects of the ingredients such as a moisturizing effect cannot be obtained sufficiently.

SUMMARY OF THE INVENTION

Accordingly, it is an object of this invention to provide a cosmetic composition which provides excellent moisturizing effect and excellent extendibility when applied to the skin, hair and the like, and exhibits excellent smoothness under dry and wet conditions and has excellent emulsion stability.

It is another object of this invention to provide a polyol glyceryl ether which is usable as an ingredient of the above cosmetic composition.

These objects have been achieved based on the following finding: a cosmetic composition which exhibits an excellent extendibility and an excellent skin moisturizing effect, which gives a refreshing feeling to users without giving greasy feel and which has excellent stability can be obtained by the combined use of (A) a nonionic amphipathic compound which has a lamellar liquid crystal structure in a wide temperature range and (B) a specific compound having a hydroxyl group.

Namely, this invention provides a cosmetic composition comprising:

(A) a nonionic amphipathic compound having in the molecule thereof at least one long chain branched alkyl or a alkenyl group and at least three hydroxyl groups, and having a lamellar liquid crystal structure at 25° C. and at 50° C. or higher; and (B) a compound represented by formula (1):

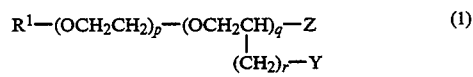

$$R^1-(OCH_2CH_2)_p-(OCH_2CH)_q-Z \qquad (1)$$
$$\phantom{R^1-(OCH_2CH_2)_p-(OCH_2CH)_q}|$$
$$\phantom{R^1-(OCH_2CH_2)_p-(OCH_2CH)_q}(CH_2)_r-Y$$

wherein $R^1$ is a hydrogen atom, a lower alkyl group or a group

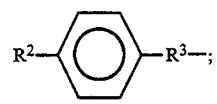

$R^2$ is a hydrogen atom, a methyl group or a methoxy group; $R^3$ is a direct bond or a saturated or unsaturated divalent hydrocarbon group having 1 to 3 carbon atoms; each Y and each Z are independently hydrogen atoms or hydroxyl groups; and p, q and r are each independently integers of 0 to 5, excepting the case where all of p, q and r are zero and Z is H, and the case where all of p, q and r are zero, $R^1$ is H and Z is OH

DETAILED DESCRIPTION OF THE INVENTION AND THE PREFERRED EMBODIMENTS

Figure 1:
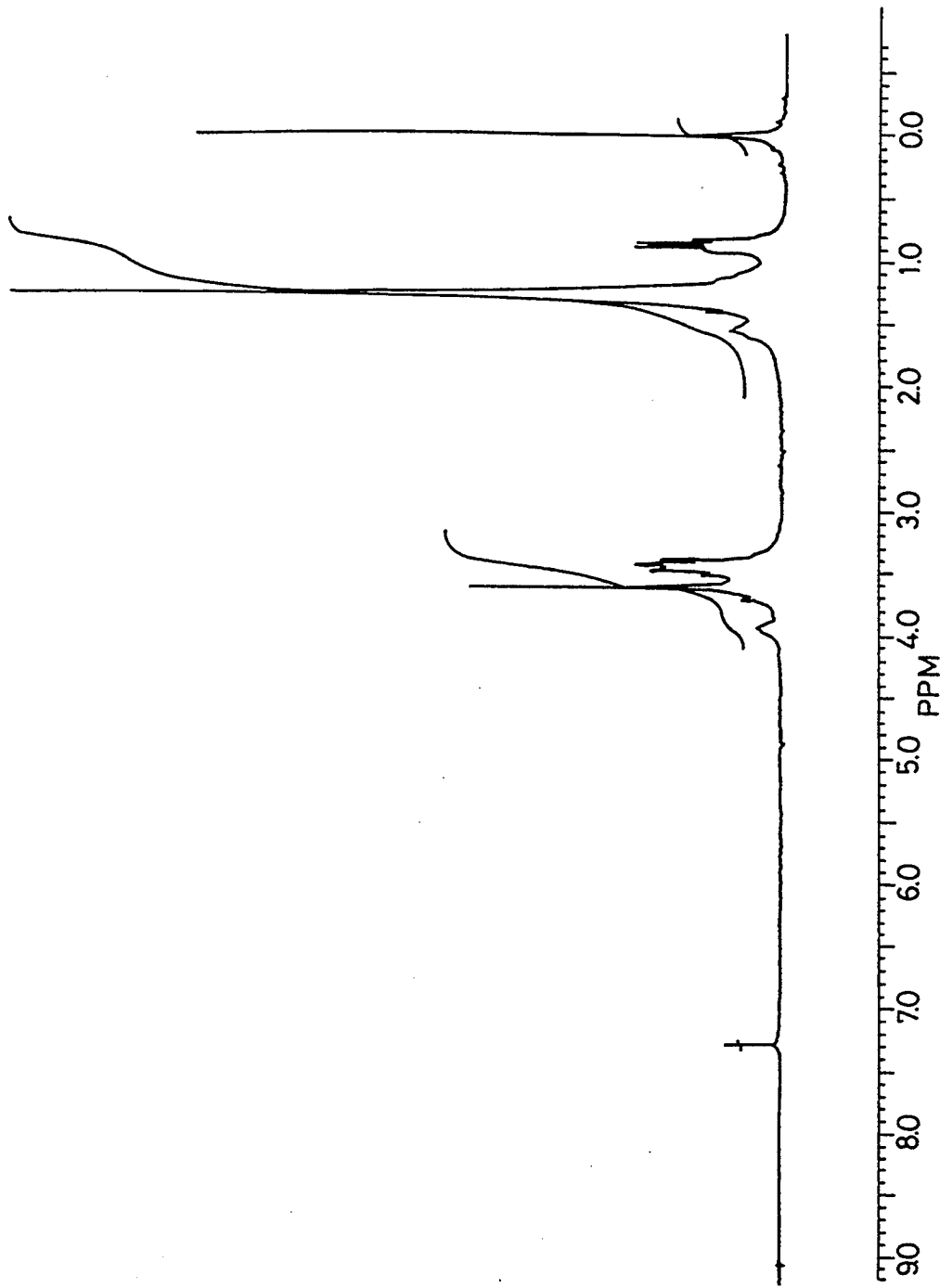
FIG. 1 is a chart showing the E spectrum of a pentaerythritol.glyceryl isostearyl monoether obtained in Synthetic Example 1.

A nonionic amphipathic compound, which is the component (A) used in the present invention, is required to have a lamellar liquid crystal structure itself at 25° C. and 50° C. or higher. The lamellar liquid crystal structure can be ascertained, for example, by X-ray diffraction or with a differential scanning calorimeter (DSC), according to the method disclosed in "The Journal of Cell Biology", Vol 12, pp 207–209 and "Surface", Vol 11, No 10, pp. 579–590. Examples of nonionic amphipathic compounds having in the molecule thereof at least one long chain ($C_9+$) branched alkyl or alkenyl group and at least three hydroxyl groups having the above-mentioned property include the following compounds (A-1), (A-2) and (A-3).

(A-1) Polyol glyceryl ethers represented by formula (2):

wherein G, A, B, x and y are as follows:

G is a trimethylolalkane residual group represented by formula (3a) or a pentaerythritol residual group represented by formula (3b):

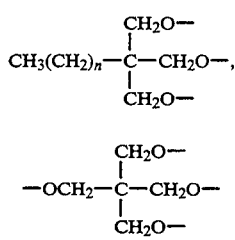

wherein n is an integer of 0–4, or a residual group obtained by removing hydrogen atoms from all the hydroxyl groups of a polyol having four or more hydroxyl groups, excepting sucrose, fructofuranose, fructopyranose, and glucopyranose.

each A is independently an alkylene group having 2–4 carbon atoms;

each B is independently a hydrogen atom or —$CH_2CH(OH)CH_2OR^4$ and/or

wherein $R^4$ is a branched alkyl or alkenyl group having 10–36 carbon atoms, provided that at least one of said B groups is —$CH_2CH(OH)CH_2OR^4$ and/or

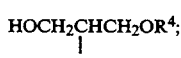

x is a number of 0–10 obtained by dividing, by y, the total mol number of alkylene oxide added to the hydroxyl groups of the trimethylolalkane or polyol; and y is the number of hydroxyl groups of the trimethylolalkane or polyol.

(A-2) Methyl branched fatty acid esters represented by formula (4):

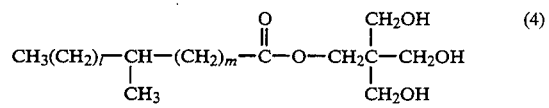

wherein l and m are integers of 0–33, and the sum of l and m is 6–33.

(A-3) A branched fatty acid glycero glycolipid represented by formula (5):

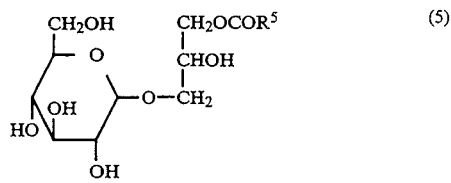

wherein $R^5$ is a group represented by

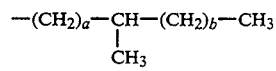

or

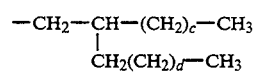

or where a and b are integers of 0–33, respectively, the sum of which is 6–33, and c and d are integers of 0–31, the sum of which is 4–31.

Among the components (A-1), a compound represented by formula (2') is a new compound which has not been disclosed in any document, and is preferred as an ingredient of the cosmetic composition according to this invention.

wherein G, A, B, x and y are as follows:

G is a trimethylolalkane residual group represented by formula (3a) or a pentaerythritol residual group represented by formula (3b):

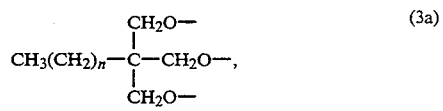

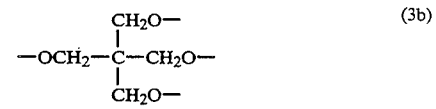

wherein n is an integer of 0–4, or a residual group obtained by removing hydrogen atoms from all the hydroxyl groups of a polyol which has four or more hydroxyl groups, excepting sucrose, fructofuranose, fructopyranose, polyglycerol and glucopyranose;

each A is independently an alkylene group having 2–4 carbon atoms;

each B is independently a hydrogen atom or —CH$_2$CH(OH)CH$_2$OR$^{4'}$ and/or

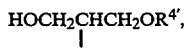

wherein R$^{4'}$ is a branched alkyl group having 10–36 carbon atoms, provided that at least one of said B groups is —CH$_2$CH(OH)CH$_2$OR$^{4'}$ and/or

x is a number of 0–10 obtained by dividing, by y, the total mol number of added alkylene oxide to the hydroxyl groups of the trimethylolalkane or polyol;

y is the number of hydroxyl groups of the trimethylolalkane or polyol.

Examples of the polyol having four or more hydroxyl groups include pentaerythritol, sorbitol, mannitol, maltitol, glucosides, polyglycerols of formula (6), erythritol, inositol, xylitol, dipentaerythritol, tripentaerythritol, heptitol, octitol, 1,2,3,4-pentatetrol, 1,3,4,5-hexanetetrol, sorbitane, mannitan, rafinose, gentianose, xylose, galactose, mannose, maltose, sorbiose, maltotriose, maltotetraose, maltopentaose, α-cyclodextrin, β-cyclodextrin, γ-cyclodextrin and their aklylene oxide adducts.

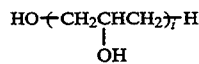 (6)

wherein i is a number of 2–20.

Examples of alkylene oxide adducts (average added mol number: 1–10 mols) of pentaerythritol, sorbitol, mannitol and the like include polyoxyethylene sorbitol, polyoxypropylene sorbitol, polyoxyethylene-polyoxypropylene sorbitol, polyoxyethylene pentaerythritol, polyoxypropylene pentaerythritol, polyoxyethylene.-polyoxypropylene pentaerythritol, polyoxyethylene mannitol, polyoxypropylene mannitol, polyoxyethylene.polyoxypropylene mannitol, polyoxyethylene maltitol, polyoxypropylene maltitol, polyoxyethylene.-polyoxypropylene maltitol.

Examples of glycosides include ones which are obtained by reacting the following substances (a) and (b) by a well known method in the presence of an acid catalyst: (a) monosaccharides such as glucose, galactose, fructose, mannose and xylose, disaccharides such as maltose, isomaltose, lactose and sucrose, or polysaccharides such as cellulose, starch and amylose; (b) lower alcohols such as methanol, ethanol and propanol, or polyols such as ethylene glycol, propylene glycol, glycerol, erythritol and sorbitol. Specifically, examples of such glycosides include alkyl glycosides such as methyl glucoside, ethyl glucoside, propyl glucoside, octyl glucoside, decyl glucoside, dodecyl glucoside, oleyl glucoside, 2-ethylhexyl glucoside, methyl maltoside and ethyl maltoside; hydroxy alkyl glycosides such as 2-hydroxypropyl glucoside, 2,3-dihydroxypropyl glucoside, 2-hydroxyethyl glucoside; alkyl ether glycosides such as methoxyethyl glucoside, ethoxyethyl glucoside; and oligo sugars such as maltitol and lactitol, whose reduction end is reduced.

Examples of the alkylene oxide adducts (average added mol number: 1–10 mols) include polyoxyethylene methyl glucoside, polyoxypropylene methyl glucoside and polyoxyethylene.polyoxypropylene methyl glucoside.

The polyglycerol represented by formula (6) is a polyglycerol which is obtained by condensing, by a well known method, a glycerol such as diglycerol, triglycerol, tetraglycerol and pentaglycerol. The polyglycerol used in this invention is a polyglycerol whose average condensation degree (i) is in a range of 2–20. When a polyglycerol having a high condensation degree is used, it may happen that sufficient effect cannot be obtained because of too high hydrophilicity. The preferred average condensation degree (i) is in a range of 2–10, and the particularly preferred average condensation degree (i) is in a range of 2–4. The polyglycerols can be used singly or as mixtures of two or more.

Examples of the alkylene group A in formulas (2) and (2') include an ethylene group, propylene group, trimethylene group and tetramethylene group.

A preferred example of the branched alkyl or alkenyl group represented by R$^4$ in formula (2) is a branched alkyl group having 16–36 carbon atoms (R4'), and a branched alkyl group having 18–24 carbon atoms is particularly preferred. The preferred branched alkyl group R$^{4'}$ is represented by formula (7),

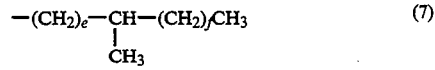

wherein e and f are integers of 0–33, respectively, and the sum of e and f is 13–33, or formula (8),

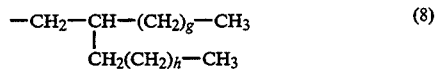

wherein g and h are integers of 0–31, respectively, and the sum of g and h is 11–31. Examples of the preferred branched alkyl group include methyl pentadecyl group, methyl hexadecyl group, methyl heptadecyl(isostearyl) group, methyl octadecyl group, methyl behenyl group, ethyl hexadecyl group, ethyl octadecyl group, ethyl behenyl group, butyl dodecyl group, butyl hexadecyl group, butyl octadecyl group, hexyl decyl group, heptyl undecyl group, octyl dodecyl group, decyl dodecyl group, decyl tetradecyl group, dodecyl hexadecyl group and tetradecyl octadecyl group.

The preferred range of x in formula (2) is 1–3, and 1 or 2 is particularly preferred. The polyol glyceryl ethers (2) are prepared by the reaction of polyols with corresponding branched alkyl or alkenyl glycidyl ethers according to the following scheme:

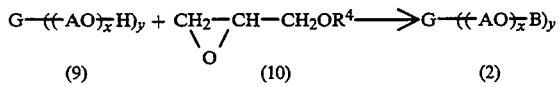

wherein A, B, G, x, y and R$^4$ have the aforementioned meanings.

Polyols (9) useful in the present invention may contain impurities other than required polyols. These polyols can be used as is when there is no practical problem, but they may be used after purification by purification techniques well-known in the art, when necessary.

For example, dipentaerythritol and tripentaerythritol are sometime included in pentaerythritol as impurities, and a little amount of glycidyl ether adducts of dipentaerythritol and tripentaerythritol are produced as by-products. When these by-products do not affect the function and quality of the final product, the pentaerythritol is used as is. When these by-products affect the quality adversely, it is preferred that a purified pentaerythritol, which is purified, for example, by crystal precipitation, be used as a starting material. Also, in the event that a little amount of reducing sugar such as glucose is included in sorbitol and mannitol, small amounts of glycidyl ether adducts of the reducing sugar are produced as by-products. When these by-products do not affect the performance and quality of the final product, the sorbitol or mannitol can be used as is. When these by-products have bad effects, it is preferred that a purified sorbitol or a purified mannitol, which are purified, for example, by crystal precipitation, be used as starting materials.

The reaction mol ratio between the polyol (9) and the branched alkyl glycidyl or alkenyl glycidyl ether (10) can properly be selected based on the etherification degree of the desired polyol glyceryl ether. For example, to obtain a polyol glyceryl ether containing a large amount of one mol adduct thereof, the ratio is generally adjusted to fall in a range of from 1.2:1.0 to 10.0:1.0 using the polyols excessively.

Taking account of the production amount of one mol adduct and the recovery of polyols, it is preferred that the ratio be in a range of from 1.5:1.0 to 5.0:1.0. Further, to obtain a polyol glyceryl ether containing a large amount of two mol adduct thereof, the ratio is generally adjusted to fall in a range of from 0.3:1.0 to 1.1:1.0 using the branched alkyl or alkenyl glycidyl ether excessively. Taking account of the production amount of two mol adduct, it is preferred that the ratio be in a range of from 0.4:1.0 to 0.8:1.0.

Although the reaction is generally carried out without any solvent, it is preferred that an organic solvent be used to promote thorough mixing of a polyol and a branched alkyl or alkenyl glycidyl ether. Examples of such organic solvents include dimethyl sulfoxide, dimethyl acetamide, dimethyl formamide, N-methyl pyrrolidone. The preferred amount of these solvents is in a range of from 0.1 to 10.0 times of the polyol.

Although an acid or a basic catalyst, which are generally known as a reaction catalyst of epoxy group, can be used as a catalyst, the acid catalysts are not preferred, because the decomposition reaction for the ether bond of the produced glycidyl etherified polyol and the dehydrating reaction for the hydroxyl group thereof occur. It is therefore preferred that basic catalysts be used. Although any kind of basic catalyst can be used, sodium hydroxide, potassium hydroxide, sodium methylate, sodium ethylate and sodium hydride are preferred from the viewpoint of reactivity and economy. The preferred amount of the basic catalyst is in a range of from 0.01 to 20.0 wt. % with respect to the polyol and a range of from 0.1 to 10.0 wt. % is particularly preferred.

The reaction is carried out at a temperature of 50°–200° C., and preferably at a temperature of 80°–150° C. Temperatures below 50° C. are not preferred because of slow reaction speed, while temperatures above 200° C. are not preferred because coloration of the product may occur.

When water exists in the reaction system, the epoxy group of a branched alkyl or alkenyl glycidyl ether is reacted with water, thereby producing a glyceryl ether. It is therefore preferred that a branched alkyl or alkenyl glycidyl ether be added for reaction after water is removed. Water can be removed by a method wherein a polyol is dissolved or dispersed in an organic solvent, and a dry nitrogen gas is passed through the solvent while heating, or a method wherein water is removed by heating under reduced pressure.

After the completion of the reaction, an organic acid such as acetic acid or citric acid, or an inorganic acid such as sulfuric acid, hydrochloric acid or phosphoric acid is added to the solvent to neutralize the solvent, and the organic solvent used in the reaction is then removed. It is preferred that the solvent be removed at a temperature of 120° C. or lower under reduced pressure to prevent the heat decomposition of the reaction product.

By the above-noted reaction, a polyol glyceryl ether (2) is obtained as a mixture of various adducts which comprises a one-mol-adduct in which one molecule of branched alkyl or alkenyl glycidyl ether (10) is added to one molecule of polyol (9), a two-mol-adduct in which two molecules of branched alkyl or alkenyl glycidyl ether (10) is added to one molecule of polyol (9) and multimol-adducts in which three or more molecules of branched alkyl or alkenyl glycidyl ether (10) is added to one molecule of polyol (9). Thus obtained polyol glyceryl ether (2) is generally used as a mixture of one-mol-adducts, two-mol-adducts and multimol adducts. If needed, the polyol glyceryl ether (2) may be purified by well known purification methods such as by silica gel column chromatography, solvent extraction and the like. Further, unreactive glycosides may sometimes be contained in the polyol glyceryl ether (2) other than the target one-mol-adducts, two-mol-adducts or multimol adducts. Although the polyol glyceryl ether (2) can be used as is when the unreactive glycosides do not bring about any practical problems, they can be removed by two layer solvent extraction using organic solvents such as ethyl acetate, methyl ethyl ketone, methyl isobutyl ketone and chloroform, by the Smith's membrane distillation or by other known purification methods, when necessary. Mixtures of one-mol-adduct, two-mol-adduct and multimol-adduct of the polyol glyceryl ether, however, can be used as the component (A) without purification when there is no practical problem.

Further, although the sum of 1 and m in formula (4) is 6–33, 10–16 is preferred from the view point of the performance as an ingredient of cosmetic compositions, and 14 is particularly preferred. It is preferred that the branched methyl group be located at the vicinity of the center of the alkyl main chain.

The methyl branched fatty acid esters (4) are prepared according to the following scheme:

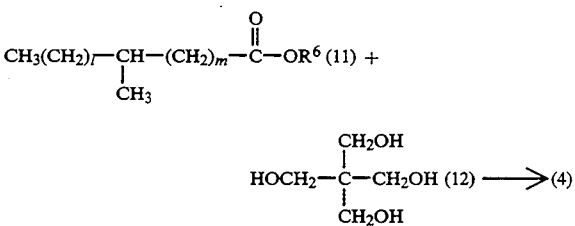

wherein 1 and m have the aforementioned meanings, and $R^6$ represents a lower alkyl group.

Namely, the compound (4) is prepared by reacting the lower alkyl ester (11) of a methyl branched fatty acid with pentaerythritol (12).

The lower alkyl esters of methyl branched fatty acid (11) useful in the reaction can be obtained by esterifying corresponding carboxylic acids by any usual method. Among the corresponding carboxylic acids, industrially obtainable are mixtures of carboxylic acids in which the sum of the number of carbon atoms of an alkyl group and the position of a branched methyl group have specific distributions. For example, in an isostearic acid having a methyl branch, which is obtained as a by-product in the preparation of an oleic acid dimer, 75 wt. % thereof is an isostearic acid whose total numbers of carbon atoms is 18 (the sum of 1 and m: 14) and the remainder is composed of isostearic acids whose total numbers of carbon atoms are 14, 16 and 20, respectively, and the branched methyl group is located at the mid-chain of alkyl (Journal of the American Oil Chem. Society, Vol. 51, p. 522 (1974)).

In this reaction, the preferred mol ratio of the lower alkyl esters (11) and the pentaerythritol (12) is $(11)/(12) = 1/1-10/1$.

Although any solvent can be used in this reaction, solvents which can dissolve both the lower alkyl esters of methyl branched fatty acid (11) and the pentaerythritol (12), for example, dimethyl formamide are preferred.

Also, an alkaline catalyst is generally used as a reaction catalyst, and, for example, sodium methylate is used by preference. Although any amount of a catalyst can be used, the preferred amount of a catalyst is in a range of 0.1–20 mol % to the lower alkyl esters of methyl branched fatty acid ester (11). This reaction is carried out at a reaction temperature of 60°–150° C.

The separation of the compound (4) from the reaction mixture is carried out by known methods, singly or in combination, e.g., solvent distillation, recrystallization and chromatography.

Also, the preferred range of a and b in formula (5) representing branched fatty acid glycero glycolipids is the same as that of the aforementioned 1 and m.

The branched fatty acid glycero glycolipids (5) can be prepared according to the following scheme:

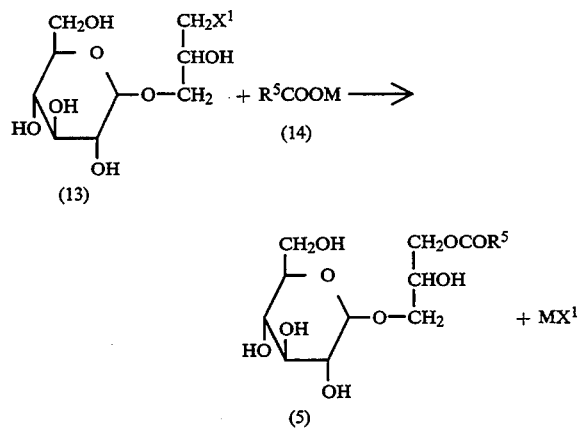

wherein $X^1$ is a halogen atom, M is a hydrogen atom or a cationic group, and $R^5$ has the aforementioned meaning.

Namely, the compound (5) is prepared by reacting the compound (13) with the fatty acid (14).

The compound (13) used in this method can easily be prepared by any well known method such as a reaction of monosaccharides or oligosaccharides and glyceryl monohalohydrin, glyceryl dihalohydrin, or epihalohydrin.

The compound (14) can be prepared, for example, by reacting a fatty acid with an alkali metal hydroxide such as sodium hydroxide or an amine in the presence of a proper solvent. Examples of the cationic group indicated by M in the compound (14) include alkali metals, an ammonium group, an alkyl ammonium group and a trialkanol amine.

In the practice of this method, the compounds (13) and (14) are reacted, for example, at a temperature of 30°–150° C., preferably at a temperature of 70°–120° C. The amount of the compound (14) used in the reaction is 0.3–3.0 times in mol to the compound (13), preferably 1.0–2.0 times in mol. When M of the compound (14) is a hydrogen atom, the reaction is carried out in the co-presence of alkaline substances. Examples of alkaline substances include alkali metal hydroxides such as sodium hydroxide and potassium hydroxide, alkali metal alcoholates and alkyl amine hydroxide.

In this reaction, a polar solvent may be used to promote thorough blending of the compounds (13) and (14), thereby smoothly carrying out the reaction. As the polar solvent useful in the reaction, one or more may be selected from dimethyl formamide, dimethyl acetamide, dimethyl sulfoxide, N-methyl pyrrolidone, pyridine and water. The amount of the solvent is not specified. In this reaction, a phase transfer catalyst may also be used to promote the reaction when necessary. Although any amount of a phase transfer catalyst can be used, the amount is usually in a range of 0.1–10 mol % to the compound (14). Examples of the phase transfer catalyst include tetraalkyl ammonium chlorides such as tetraethyl ammonium bromide, tetrapropyl ammonium bromide, tetrabutyl ammonium bromide, tetraheptyl ammonium bromide, tetrahexyl ammonium bromide, N,N,N-trimethyl-N-octyl ammonium chloride, N,N,N-trimethyl-N-decyl ammonium chloride, N,N,N-trimethyl-N-dodecyl ammonium chloride, N,N,N-trimethyl-N-hexadecyl ammonium chloride, N,N,N-trimethyl-N-octadecyl ammonium chloride, N,N-dimethyl-N,N-dihexadecyl ammonium chloride and N,N-dimethyl-N,N-dioctadecyl ammonium chloride.

The reaction product generally contains inorganic salts and unreacted compounds (13) and (14) as by-products other than the target glycero glycolipids (5). Although the reaction product can be used as is when the purpose allows, it can be purified by well known methods such as partition chromatography, adsorption chromatography and recrystallization, when a product having a higher purity is required.

The compounds (A-1), (A-2) and (A-3) obtained from by the above-mentioned reaction are thermotropic liquid crystals which take lamellar liquid crystal structures in a wide temperature range, and have excellent properties such as a property of uniformly dispersing as lamellar liquid crystals when mixed with water.

The component (A) can be used singly or in combination of two or more, and the preferred incorporation amount in the cosmetic composition of this invention is generally 0.01–80 wt. %, preferably 0.1–60 wt. %.

Examples of the component (B) used in this invention include glycerol, 1,3-butylene glycol, propylene glycol, dipropylene glycol, ethylene glycol, diethylene glycol, polyethylene glycol, isoprene glycol, sorbitol, diethylene glycol monoethyl ether, diethylene glycol monobutyl ether, isopropyl alcohol, ethyl alcohol, benzyl alcohol, benzyl oxyethanol, among which glycerol, propylene glycol and diethylene glycol monoethyl ether are particularly preferred.

The component (B) can be used singly or in combination of two or more, and the preferred incorporation amount in the cosmetic composition of this invention is generally 0.1–90 wt. %, preferably 0.5–50 wt. %.

Further, a surfactant may additionally be used to enhance the effects of the cosmetic composition of this invention. Any one of nonionic surfactants, cationic surfactants, anionic surfactants and amphoteric surfactants can be used as the surfactant. In particular, nonionic surfactants are preferred for cosmetic compositions for the skin, and anionic surfactants, nonionic surfactants and amphoteric surfactants are preferred for detergents for the skin and hair, while cationic surfactants are preferred for hair cosmetic compositions such as hair rinses and hair styling agents. Examples of nonionic surfactants include polyoxyethylene alkyl ethers, polyoxyethylene alkyl phenyl ethers, polyoxyethylene fatty acid esters, sorbitan fatty acid esters, polyoxyethylene sorbitan fatty acid esters, fatty acid monoglycerides, sucrose fatty acid esters, higher fatty acid alkanol amides. Quaternary ammonium salts are typical examples of cationic surfactants. Although any one of quaternary ammonium salts generally incorporated into cosmetic compositions is preferred, it is preferred to incorporate in cosmetic compositions one or more branched chain quaternary ammonium salts which are represented by the following formulas (15) and (16), and are disclosed in Japanese Patent Application Laid-Open No. 61-267505.

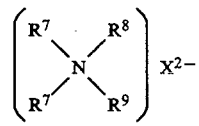

(15)

wherein $R^7$ is an alkyl group selected from the group consisting of a branched chain alkyl group represented by (a):

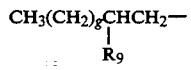

or a straight chain alkyl group represented by (b): $-(CH_3-CH_2)_h$, wherein $R^9$ is a methyl group or an ethyl group, g and h are numbers which make the total number of the carbon atoms of alkyl group be 8–16, and wherein the branch ratio (a)/((a)+(b)) of the group $R^7$ is 10–100 wt. %, $R^8$ and $R^9$ are groups selected from the group consisting of a benzyl group, alkyl group having 1–3 carbon atoms or hydroxy alkyl group, and $X^{2-}$ is a halogen ion or an organic anion.

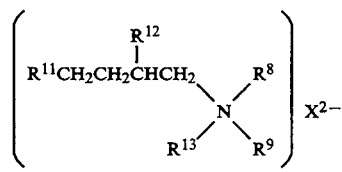

(16)

wherein $R^{11}$ and $R^{12}$ are alkyl groups having 2–12 carbon atoms, $R^{13}$ is a group

or an alkyl group having 1–3 carbon atoms, and $R^8$, $R^9$ and $X^{2-}$ have the same meaning as those in formula (15).

Examples of anionic surfactants include straight or branched chain alkyl benzene sulfonic acid salts, alkyl or alkenyl sulfates, alkyl or alkenyl ether sulfates to which ethylene oxide and/or propylene oxide are added, olefin sulfonates, alkane sulfonates, saturated or unsaturated fatty acid salts, alkyl or alkenyl ether carboxylic acid salts to which ethylene oxide and/or propylene oxide are added, α-sulfo fatty acid salt esters, amino acid surfactants, phosphate surfactants, sulfosuccinate surfactants, taurine surfactants, amide ether sulfate surfactants. Examples of amphoteric surfactants include sulfonate amphoteric surfactants and betaine amphoteric surfactants. The incorporation amount of these surfactants is 0.01–30% of the total amount of the composition, preferably 0.1–10%.

The cosmetic compositions of this invention can optionally contain other compatible ingredients which are generally incorporated into cosmetic compositions, drugs, foods, etc. Examples of such optional ingredients are higher alcohols having a straight or branched chain alkyl or alkenyl group; hydrocarbons such as liquid paraffin, vaseline and solid paraffin; silicone derivatives such as dimethyl polysiloxane, polyether modified silicone, amino modified silicone, cyclic silicone, alkoxy modified silicone; lanolin derivatives such as liquid lanolin, lanolin fatty acid; phospholipids such as lecithin; sterols such as cholesterol and derivatives thereof; collagen decomposition peptide derivatives; perfluoropolyethers; oils and fats such as higher alcohol higher fatty acid esters, higher fatty acids, long chain amidoamines having an alkyl or alkenyl group; animal or vegetable-origin fats and oils such as mink oil and olive oil; antidandruffs, germicides, and vitamins; antiseptics such as paraben; viscosity modifiers such as water-soluble polymers; colorants such as dyes and pigments; ultraviolet ray absorbers; astringents; perfumes; and ingredients listed in "Encyclopedia of Conditioning Rinse Ingredients" (Micelle Press, 1987) and "Encyclopedia of Shampoo Ingredients" (Micelle Press, 1985) and "Saishin Keshohin Kagaku" (Yakuji Nipposha, 1988). They can be used in such an amount that will not impede the effects of this invention.

The cosmetic compositions of this invention are prepared according to well known methods using the mentioned ingredients. The compositions of this invention are suitable for formulating skin care compositions such as O/W emulsion-type cosmetic compositions, W/O emulsion-type cosmetic compositions and an oil type cosmetic compositions; make-up cosmetic compositions such as lipsticks and foundations; skin detergents; body treatments; hair cosmetic compositions such as shampoos, hair rinses, hair treatments, hair creams, styling lotions, styling mousses, conditioning mousses, hair sprays, hair liquids and styling gels; skin care cosmetic compositions such as skin creams, skin milks and skin lotions; and bathing agents.

By the synergistic effect of the components (A) and (B), the cosmetic compositions of this invention provide excellent moisturizing effect and excellent extendability without giving an oily feel to users. In particular, when applied to the hair, the cosmetic compositions also exhibit excellent smoothness even under wet conditions without giving a sticky feel to users. The cosmetic compositions also have excellent emulsion stability.

EXAMPLES

This invention will now be described by way of synthetic examples, comparative examples, test examples and examples, which should, however, not be construed as limiting the invention.

Synthetic Example 1

82 g of pentaerythritol, 200 g of dimethyl sulfoxide and 1 g of sodium hydroxide were placed in a 500 ml flask and heated at 105° C. to form a solution, through which dried nitrogen gas was passed for removing humidity from the reaction system by expelling about 20 g of water and dimethyl sulfoxide. 39 g of isostearylglycidyl ether was added thereto dropwise over 1 hour, and reaction was allowed to proceed at 105° C. for 4 hours under agitation.

After the termination of the reaction, 1.5 g of acetic acid was added to the reaction mixture to neutralize the catalyst. Dimethyl sulfoxide was distilled off under reduced pressure at 80° C. The residue was mixed with 99% ethanol, and unreacted pentaerythritol which was precipitated was filtered out.

From the obtained filtrate, ethanol was evaporated under reduced pressure, and the residue was mixed with 500 ml of water and 500 ml of ethyl acetate for ethyl acetate extraction. From the ethyl acetate-soluble fraction, solvent was evaporated to obtain 63 g of a primary purified product, which is a pale yellow pentaerythritol.isostearyl glycidyl ether adduct.

This primary purified product was further purified by silica gel column chromatography (acetone:hexane=2:1) to elute a target pentaerythritol.glyceryl isostearyl monoether fraction. The elution fraction was collected and solvent was evaporated to finally obtain 16 g of pentaerythritol.glyceryl isostearyl monoether (yield: 30%).

Figure 2:
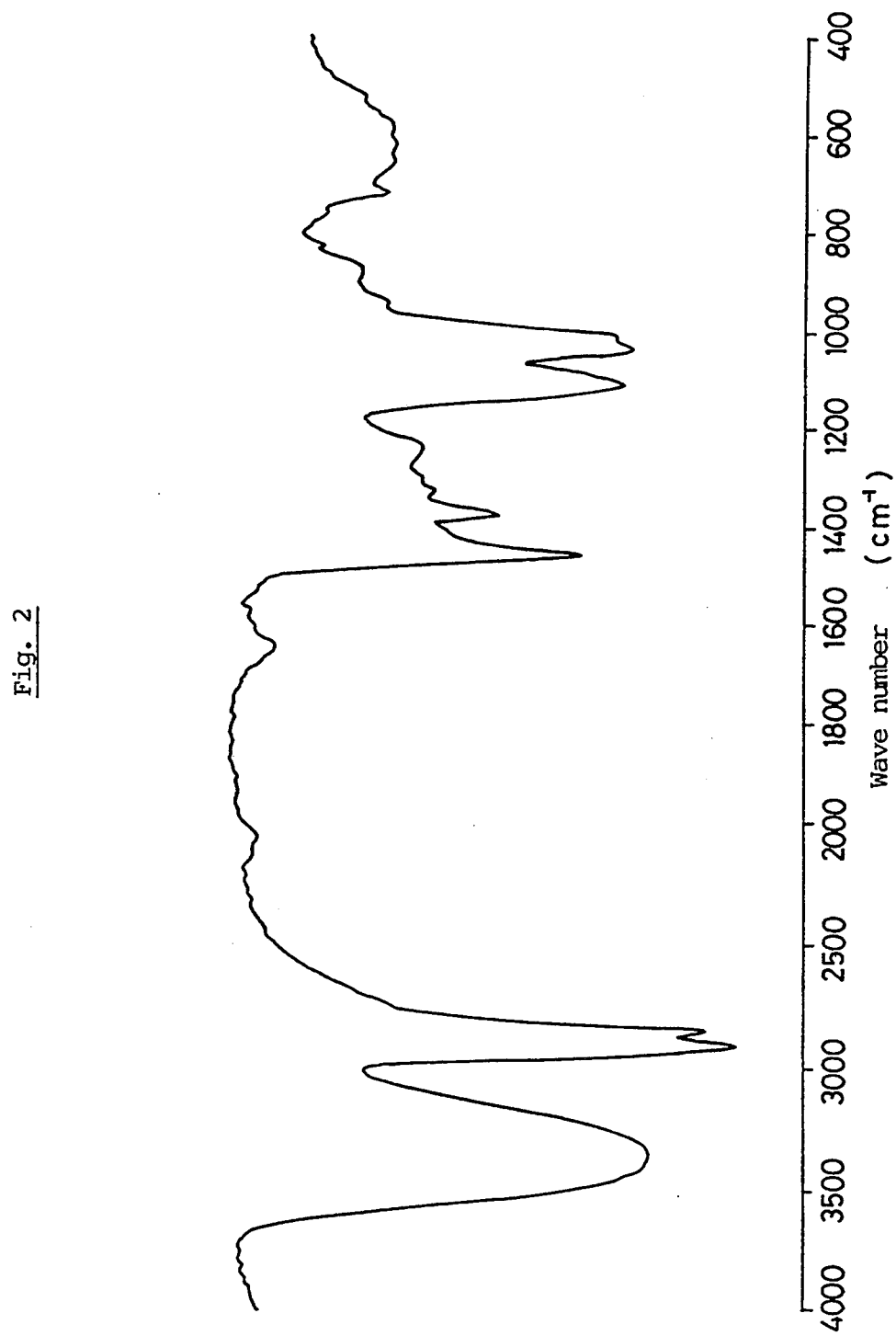
FIG. 2 is a chart showing the IR spectrum of the pentaerythritol.glyceryl isostearyl monoether obtained in Synthetic Example 1.

The NMR spectrum and the IR spectrum of the obtained compound are shown in FIG. 1 and FIG. 2, respectively.

Hydroxyl value: 482 (Calculated: 486)

NMR (CDCl$_3$): $\delta$ (ppm) 3.95 (1H, m, —OCH$_2$—CHOH—CH$_2$O—), 3.67(6H, s, —C(CH$_2$OH)$_3$), 3.46 (8H, m, —OCH$_2$—), 1.30~1.59(29H, b, —CH$_2$, —OH—), 0.88(6H, m, —CH$_3$)

IR (liquid film) cm$^{-1}$: $\nu_{O-H}$(—OH)3200~3400; $\nu_{O-H}$ (extension)(—CH—, —CH$_2$—, —CH$_3$) 2850, 2920; $\nu_{O-H}$ (deformation)(—CH—, —CH$_2$—, —CH$_3$) 1375, 1460; $\nu_{C-O}$(—C—O—) 1110, 1035, 1010

Synthetic Example 2

91 g of sorbitol, 100 g of N-methyl pyrrolidone and 1 g of sodium hydroxide were placed in a 300 ml flask and heated at 100° C. to form a solution, through which dried nitrogen gas was passed for removing humidity from the reaction system by expelling about 10 g of water and N-methyl pyrrolidone. 33 g of isostearylglycidyl ether was added thereto dropwise over 2 hours, and reaction was allowed to proceed at 110° C. for 4 hours under agitation.

After the termination of the reaction, 1.5 g of acetic acid was added to the reaction mixture to neutralize the catalyst. N-methyl pyrrolidone was distilled off under reduced pressure at 80° C. The residue was mixed with 500 g of acetone, and unreacted sorbitol which was precipitated was filtered out. From the obtained filtrate, acetone was evaporated under reduced pressure to obtain 42 g of a primary purified product, sorbitol.isostearyl glycidyl ether adduct.

This primary purified product was further purified by silica gel column chromatography (chloroform:methanol=5:1) to elute a target sorbitol.glyceryl isostearyl monoether fraction. The elution fraction was collected and solvent was evaporated to finally obtain 20 g of sorbitol.glyceryl isostearyl monoether (yield: 39%).

Hydroxyl value: 664 (Calculated: 663)

NMR (CDCl$_3$): $\delta$ (ppm) 3.95~3.94(15H, m, —O—CH$_2$—, O—CH—), 1.34~1.58(29H, b, —CH$_2$—, —CH—), 0.86(6H, m, —CH$_3$)

IR (liquid film) cm$^{-1}$: $\nu_{O-H}$(—OH) 3200~3400; $\nu_{O-H}$ (extension)(—CH—, —CH$_2$—, —CH$_3$) 2840, 2910; $\nu_{O-H}$ (deformation)(—CH—, —CH$_2$—, —CH$_3$) 1370, 1455; $\nu_{C-O}$(—C—O—) 1030~1110

Synthetic Example 3

91 g of mannitol, 50 g of dimethyl sulfoxide and 0.8 g of sodium hydroxide were placed in a 300 ml flask and heated at 120° C. to form a solution, through which dried nitrogen gas was passed for removing humidity from the reaction system by expelling about 10 g of water and dimethyl sulfoxide. 35 g of 2-octyldodecyl glycidyl ether was added thereto dropwise over 2 hours, and reaction was allowed to proceed at 120° C. for 6 hours under agitation.

After the termination of the reaction, 1.2 g of acetic acid was added to the reaction mixture to neutralize the catalyst. Dimethyl sulfoxide was distilled off under reduced pressure at 80° C.

The residue was mixed with 500 g of water and then extracted with 1000 ml of methyl ethyl ketone (500 ml×2). The obtained methyl ethyl ketone layer was dried over Glauber's salt, followed by filtration and distillation of the solvent to obtain 53 g of a primary purified mannitol.2-octyldodecyl-glycidyl ether adduct.

This primary purified product was further purified by silica gel column chromatography (chloroform:methanol=5:1) to elute a target mannitol-glyceryl 2-octyldodecyl monoether fraction. The elution fraction was collected and solvent was evaporated to finally obtain 29 g of mannitol.glyceryl 2-octyldodecyl monoether (yield: 46%).

Hydroxyl value: 625 (Calculated: 628)

NMR (COCl$_3$): $\delta$ (ppm) 3.34~3.96(15H, m, —O—CH$_2$—, O—CH—), 1.33~1.59(33H, b, —CH$_2$—, —CH—), 0.87(6H, m, —CH$_3$)

IR (liquid film) cm$^{-1}$: $\nu_{O-H}$(—OH) 3200~3400; $\nu_{C-H}$ (extension)(—CH—, —CH$_2$—, —CH$_3$) 2860, 2930; $\nu_{C-H}$ (deformation)(—CH—, —CH$_2$—, —CH$_3$) 1380,1440; $\nu_{C-O}$(—C—O—) 1030~1120

Comparative Example 1

70 g of pentaerythritol, 200 g of dimethyl sulfoxide and 1 g of sodium hydroxide were placed in a 500 ml flask and heated at 100° C. to form a solution, through which dried nitrogen gas was passed for removing humidity from the reaction system by expelling about 20 g of water and dimethyl sulfoxide. 33 g of stearyl glycidyl ether was added thereto dropwise over 2 hours, and reaction was allowed to proceed at 110° C. for 5 hours under agitation.

After the termination of the reaction, 1.5 g of acetic acid was added to the reaction mixture to neutralize the catalyst. Dimethyl sulfoxide was completely distilled off under reduced pressure at 80° C. The residue was mixed with 500 g of acetone, and unreacted pentaerythritol which was precipitated was filtered out. From the obtained filtrate, acetone was evaporated under reduced pressure to obtain 45 g of a primary purified product, pentaerythritol.stearyl glycidyl ether adduct.

This primary purified product was further purified by silica gel column chromatography (hexane:acetone=2:1) to elute a target pentaerythritol.glyceryl stearyl monoether fraction. The elution fraction was collected and solvent was evaporated to finally obtain 22 g of pentaerythritol.glyceryl stearyl monoether (yield: 47%).

It was confirmed by NMR and IR spectrum analyses that the obtained compound was pentaerythritol.glyceryl stearyl monoether.

Test Example 1

The polyol glyceryl ethers obtained in Synthetic Examples 1–3 of the present invention and conventionally known compounds were tested in terms of properties at room temperature and dispersibility in water (concentration: 5% by weight). The results are shown in Table 1.

Evaluation Method

Properties at room temperature were checked by visual judgement or with a polarizing microscope. Dispersibility in water was tested in the following manner: 1 g of a test sample was collected in a 30 ml vial, to which ion-exchanged water was added so as to make the sample concentration 5% by weight. The sample vial was agitated for 1 minute, followed by being allowed to stand for 5 minutes, then dispersibility was observed by the naked eye.

TABLE 1

| Tested Compounds | Property (room temp.) | Dispersibility in water |
|---|---|---|
| Present invention | | |
| Pentaerythritol.glyceryl isostearyl monoether (Syn. Ex. 1) | Liquid crystal | Uniform dispersion |
| Sorbitol.glyceryl isostearyl monoether (Syn. Ex. 2) | Liquid crystal | Uniform dispersion |
| Mannitol.glyceryl 2-octyldodecyl monoether (Syn. Ex. 3) | Liquid crystal | Uniform dispersion |
| Comparative compounds | | |
| Pentaerythritol.glyceryl stearyl monoether (Comp. Ex. 1) | Solid | Solid/liquid separation |
| Stearyl monoglyceryl ether | Solid | Solid/liquid separation |
| Isostearyl alcohol | Liquid | Liquid/liquid separation |

Text Example 2

The compounds obtained in Synthetic Examples 1–3 and Comparative Example 1 and conventionally known compounds were used to prepare the hair rinse compositions shown in Table 2, and their rinsing performance was investigated. The results are also shown in Table 2.

Preparation

To 70° C. water were added ingredients which were heated at 70° C. and dissolved in advance, and stirred to mix, followed by cooling down to room temperature while stirring to prepare hair rinse compositions.

Evaluation method 20 g of sample hair (15 cm long) of Japanese women who had never experienced cold perming or bleaching was provided. The hair tress was shampooed with a commercially available shampoo containing an anionic surfactant as a major component, then 2 g of a hair rinse composition shown in Table 2 was uniformly applied to the hair. Rinsing under running water was conducted for 30 seconds, followed by towel-drying. The hair tress in the moistened state was organoleptically evaluated in terms of softness, smoothness and reduced greasiness. The evaluation standards are as follows:

A: Excellent
B: Good
C: Moderate
D: Inferior

TABLE 2

| | Present examples | | | Comparative examples | | |
|---|---|---|---|---|---|---|
| Component (wt. %) | 1 | 2 | 3 | 1 | 2 | 3 |
| Pentaerythritol.glyceryl isostearyl monoether (Syn. Ex. 1) | 3.0 | — | — | — | — | — |
| Sorbitol.glyceryl isostearyl monoether (Syn. Ex. 2) | — | 3.0 | — | — | — | — |
| Mannitol.glyceryl 2-octyldodecyl monoether (Syn. Ex. 3) | — | — | 3.0 | — | — | — |
| Pentaerythritol.glyceryl stearyl monoether (Comp. Ex. 1) | — | — | — | 3.0 | — | — |
| Stearyl glyceryl ether | — | — | — | — | 3.0 | — |
| Isostearyl alcohol | — | — | — | — | — | 3.0 |
| Stearyl trimethyl ammonium chloride | 2.0 | 2.0 | 2.0 | 2.0 | 2.0 | 2.0 |
| Ion-exchanged water | 95.0 | 95.0 | 95.0 | 95.0 | 95.0 | 95.0 |
| Evaluation Softness | A | A | A | B | C | C |
| Smoothness | A | A | A | C | B | B |
| Reduced greasiness | A | A | A | B | C | D |

Synthetic Example 4

97 g Of methyl glucoside, 200 g of dimethyl sulfoxide and 1 g of sodium hydroxide were placed in a 500 ml flask and heated at 105° C. to form a solution, through which dried nitrogen gas was passed for removing humidity from the reaction system by expelling about 20 g of water and dimethyl sulfoxide. 33 g of isostearylglycidyl ether was added dropwise thereto over 4 hours, and reaction was allowed to proceed at 105° C. for 5 hours under agitation.

After the termination of the reaction, 1.5 g of acetic acid was added to the reaction mixture to neutralize the catalyst. Dimethyl sulfoxide was distilled off under reduced pressure at 80° C. The residue was mixed with 99% ethanol, and unreacted methyl glucoside which was precipitated was filtered out. From the obtained filtrate, ethanol was evaporated under reduced pressure, and the residue was mixed with 500 ml of water and 500 ml of ethyl acetate for ethyl acetate extraction. From the ethyl acetate-soluble fraction, solvent was evaporated to obtain 49 g of a primary purified product, which is a pale yellow methyl glucoside.isostearyl glycidyl ether adduct.

This primary purified product was further purified by silica gel column chromatography (acetone:hexane=4:1) to elute a target methyl glucoside-glyceryl isostearyl monoether fraction. The elution fraction was collected and solvent was evaporated to finally obtain 16 g of methyl glucoside.glyceryl isostearyl monoether.

Hydroxyl value: 436 (Calculated: 432)

NMR (CDCl$_3$): δ (pm) 4.75(1H, d, —O—CH—OCH$_3$), 3.95(1H, m, —OCH$_2$—CHOH—CH$_2$O—), 3.77~3.35(12H, m, —OCH$_2$—, —OCH—), 3.24(3H, s, —OCH$_3$), 1.30~1.59(29H, b, —CH$_2$—, —CH—), 0.85(6H, m, —CH$_3$)

IR (liquid film) cm$^{-1}$: $v_{O-H}$(—OH) 3200~3400; $v_{C-H}$ (extension)(—CH—, —CH$_2$—, —CH$_3$) 2840, 2915; $v_{C-H}$(deformation)(—CH—, —CH$_2$, —CH$_3$) 1375,1460; $v_{C-O}$(—C—O) 1110, 1035, 1005

Synthetic Example 5

104 g of ethyl glucoside, 100 g of N-methyl pyrrolidone and 1 g of sodium hydroxide were placed in a 300 ml flask and heated at 110° C. to form a solution, through which dried nitrogen gas was passed for removing the humidity from the reaction system by expelling about 10 g of water and N-methyl pyrrolidone. 33 g of isostearylglycidyl ether was added dropwise thereto over 2 hours, and reaction was allowed to proceed at 110° C. for 4 hours under agitation.

After the termination of the reaction, 1.5 g of acetic acid was added to the reaction mixture to neutralize the catalyst. N-methyl pyrrolidone was distilled off under reduced pressure at 80° C. The residue was mixed with 500 g of acetone, and unreacted ethyl glucoside which was precipitated was filtered out. From the obtained filtrate, acetone was evaporated under reduced pressure to obtain 50 g of a primary purified product, ethyl glucoside.isostearyl glydidyl ether adduct.

This primary purified product was further purified by silica gel column chromatography (hexane:acetone=5:1) to elute a target ethyl glucoside.glyceryl isostearyl monoether fraction. The elution fraction was collected and solvent was evaporated to finally obtain 20 g of ethyl glucoside.glyceryl isostearyl monoether. Hydroxyl value: 420 (Calculated: 420)

NMR (CDCl$_3$): δ (ppm) 4.82(1H, d, —O—CH—OCH$_3$), 3.94(1H, m, —OCH$_2$—CHOH—CH$_2$O—), 3.77~3.50(12H, m, —OCH$_2$—, —OCH—), 3.40(2H, q, —OCH$_2$CH$_3$), 1.30~1.60(32H, b, —CH$_2$—, —CH—), 0.85(6H, m, —CH$_3$)

IR (liquid film) cm$^{-1}$: $v_{O-H}$(—OH) 3200~3400; $v_{C-H}$ (extension)(—CH—, —CH$_2$—, —CH$_3$) 2840, 2910; $v_{C-H}$ (deformation)(—CH—, —CH$_2$—, —CH$_3$) 1370,1455; $v_{C-O}$(—C—O—) 1030, 1110

Synthetic Example 6

194 g of methyl glucoside, 400 g of dimethyl sulfoxide and 2.8 g of potassium hydroxide were placed in a 300 ml flask and heated at 120° C. to form a solution, through which dried nitrogen gas was passed for removing humidity from the reaction system by expelling about 50 g of water and dimethyl sulfoxide. 33 g of 2-heptyl undecyl glycidyl ether was added dropwise thereto over 2 hours, and reaction was allowed to proceed at 120° C. for 6 hours under agitation.

After the termination of the reaction, 3 g of acetic acid was added to the reaction mixture to neutralize the catalyst. Dimethyl sulfoxide was distilled off under reduced pressure at 80° C. The residue was mixed with 1000 ml of ethanol, and methyl glucoside which was precipitated was filtered out. From the obtained filtrate, ethanol was evaporated to obtain 56 g of a primary purified product, methyl glucoside.2-heptyl undecyl glycidyl ether adduct.

This primary purified product was further purified by silica gel column chromatography (hexane:acetone=4:1) to elute a target methyl glucoside.glyceryl 2-heptyl undecyl monoether fraction. The elution fraction was collected and solvent was evaporated to finally obtain 20 g of methyl glucoside.glyceryl 2-heptyl undecyl monoether.

Hydroxyl value: 438 (Calculated: 432)

NMR(CDCl$_3$): δ (ppm) 4.90(1H, d, —O—CH—OCH$_3$), 3.88(1H, m, —OCH$_2$—CHOH—CH$_2$O—), 3.74~3.36(12H, m, —OCH$_2$—, —OCH—), 3.20(3H, s, —OCH$_3$), 1.68~1.23(29H, b, —CH$_2$—, —CH—), 0.79(6H, m, —CH$_3$)

IR (liquid film) cm$^{-1}$: $v_{O-H}$(—OH) 3200~3400; $v_{C-H}$ (extension)(—CH—, —CH$_2$—, —CH$_3$) 2860, 2930; $v_{C-H}$ (deformation)(—CH—, —CH$_2$—, —CH$_3$) 1380,1440; $v_{C-O}$(—C—O—) 1130, 1040

Synthetic Example 7

18 g of methyl maltoside, 200 g of dimethyl sulfoxide and 1 g of sodium hydroxide were placed in a 500 ml flask and heated at 105° C. to form a solution, through which dried nitrogen gas was passed for removing the humidity from the reaction system by expelling about 20 g of water and dimethyl sulfoxide. 35 g of 2-octyldodecyl glycidyl ether was added dropwise thereto over 4 hours, and reaction was allowed to proceed at 105° C. for 5 hours under agitation.

After the termination of the reaction, 1.5 g of acetic acid was added to the reaction mixture to neutralize the catalyst. Dimethyl sulfoxide was distilled off under reduced pressure at 80° C. The residue was mixed with 99% ethanol, and unreacted methyl maltoside which was precipitated was filtered out. From the obtained filtrate, ethanol was evaporated under reduced pressure to obtain 19 g of a primary purified product, methyl maltoside.2-octyldodecyl glycidyl ether adduct.

This primary purified product was further purified by silica gel column chromatography (chloroform:methanol=2:1) to elute a target methyl maltoside.glyceryl 2-octyldodecyl monoether fraction. The elution fraction was collected and solvent was evaporated to finally obtain 8 g of methyl maltoside.glyceryl 2-octyldodecyl monoether. Hydroxyl value: 560 (Calculated: 553)

NMR(CDCl$_1$): δ (ppm) 5.01~4.85(2H, m, —O—CH—OCH$_3$), 3.93(1H,m, —OCH$_2$—CHOH—CH$_2$O—), 3.75~3.40(17H, m, —OCH$_2$—, —OCH—), 3.25(3H, s, —OCH$_3$), 1.65~1.20(33H, b, —CH$_2$—, —CH—), 0.80(6H, m, —CH$_3$), IR (liquid film) cm$^{-1}$: $v_{O-H}$(—OH) 3200~3400; $v_{C-H}$ (extension)(—CH—, —CH$_2$—, —CH$_3$) 2850, 2920; $v_{C-H}$ (deformation)(—CH—, —CH$_2$—, —CH$_3$) 1375,1460; $v_{C-O}$(—C—O—) 1110, 1035, 1010

Synthetic Example 8

69 g of maltitol, 400 g of N-methyl pyrrolidone and 2 g of sodium hydroxide were placed in a 300 ml flask and heated at 110° C. to form a solution, through which dried nitrogen gas was passed for removing the humidity from the reaction system by expelling about 10 g of water and N-methyl pyrrolidone. 38 g of 2-decyl tetradecyl glycidyl ether was added dropwise thereto over 2 hours, and reaction was allowed to proceed at 110° C. for 4 hours under agitation.

After the termination of the reaction, 5 g of phosphoric acid was added to the reaction mixture to neutralize the catalyst. N-methyl pyrrolidone was distilled off under reduced pressure at 80° C. The residue was mixed with 500 g of acetone, and unreacted maltitol which was precipitated was filtered out. From the obtained filtrate, acetone was evaporated under reduced pressure to obtain 83 g of a primary purified product, maltitol-2-decyl tetradecyl glycidyl ether adduct.

This primary purified product was further purified by silica gel column chromatography (chloroform:methanol=2:1) to elute a target maltitol.glyceryl 2-decyl tetradecyl monoether fraction. The elution fraction was collected and solvent was evaporated to finally obtain 20 g of maltitol-glyceryl 2-decyl tetradecyl monoether.

Hydroxyl value: 663 (Calculated: 670)

NMR(CDCl$_3$): $\delta$ (ppm) 4.90(1H, d, —O—CH—OCH$_3$), 3.96(1H, m, —OCH$_2$—CHOH—CH$_2$O—), 3.78~3.42(20H, m, —OCH$_2$—, —OCH—), 1.30~1.59(41H, b, —CH$_2$—, —CH—), 0.81(6H, m, —CH$_3$)

IR (liquid film) cm$^{-1}$: $\nu_{O-H}$(—OH) 3200~3400; $\nu_{C-H}$ (extension)(—CH—, —CH$_2$—, —CH$_3$) 2830, 2910; $\nu_{C-H}$ (deformation)(—CH—, —CH$_2$—, —CH$_3$) 1370,1450; $\nu_{C-O}$(—C—O—) 1030, 1110

Synthetic Example 9

25 g of 2,3-dihydroxypropyl glucoside, 50 g of dimethyl sulfoxide and 1.4 g of potassium hydroxide were placed in a 300 ml flask and heated at 120° C. to form a solution, through which dried nitrogen gas was passed for removing the humidity from the reaction system by expelling about 5 g of water and dimethyl sulfoxide. 16 g of isostearyl glycidyl ether was added dropwise thereto over 2 hours, and reaction was allowed to proceed at 120° C. for 6 hours under agitation.

After the termination of the reaction, 3 g of acetic acid was added to the reaction mixture to neutralize the catalyst. Dimethyl sulfoxide was distilled off under reduced pressure at 80° C. The residue was mixed with 500 ml of water and 1000 ml of methylethyl ketone. From the obtained methylethyl ketone layer, methylethyl ketone was evaporated under reduced pressure to obtain 17 g of a primary purified product, 2,3-dihydroxypropyl glucoside.isostearylglycidyl ether adduct.

This primary purified product was further purified by silica gel column chromatography (hexane:acetone=2:1) to elute a target 2,3-dihydroxypropyl glucoside.glyceryl isostearyl monoether fraction. The elution fraction was collected and solvent was evaporated to finally obtain 7 g of 2,3-dihydroxypropyl glucoside.glyceryl isostearyl monoether.

Hydroxyl value: 578 (Calculated: 580)

NMR(CDCl$_3$): $\delta$ (ppm) 4.88(1H, d, —O—CH—OCH$_3$), 4.01~3.86(2H, m, —OCH$_2$—CHOH—CH$_2$O—), 3.75~3.46(17H, m,—OCH$_2$—, —OCH—), 1.27~1.73(29H, b, —CH$_2$—, —CH—), 0.85(6H, m, —CH$_3$)

IR (liquid film) cm$^{-1}$: $\nu_{O-H}$(—OH) 3200~3400; $\nu_{C-H}$ (extension)(—CH—, —CH$_2$—, —CH$_3$) 2860, 2920; $\nu_{C-H}$ (deformation)(—CH—, —CH$_2$—, —CH$_3$) 1370, 1440; $\nu_{C-O}$(—C—O) 1040, 1120

Comparative Example 2

97 g of methyl glucoside, 200 g of dimethyl sulfoxide and 1 g of sodium hydroxide were placed in a 500 ml flask and heated at 105° C. to from a solution, through which dried nitrogen gas was passed for removing the humidity from the reaction system by expelling about 20 g of water and dimetyl sulfoxide. 33 g of stearyl glycidyl ether was added dropwise thereto over 4 hours, and reaction was allowed to proceed at 105° C. for 5 hours under agitation.

After the termination of the reaction, 1.5 g of acetic acid was added to the reaction mixture to neutralize the catalyst. Dimethyl sulfoxide was distilled off under reduced pressure at 80° C. The residue was mixed with 99% ethanol, and unreacted methyl glucoside which was precipitated was filtered out. From the obtained filtrate, ethanol was evaporated under reduced pressure, and the residue was mixed with 500 ml of water and 500 ml of ethyl acetate for ethyl acetate extraction. From the ethyl acetate-soluble fraction, solvent was evaporated to obtain 47 g of a primary purified product, which is a pale yellow methyl glucoside.stearyl glycidyl ether adduct.

This primary purified product was further purified by silica gel column chromatography (acetone:hexane=4:1) to elute a target methyl glucoside-glyceryl stearyl monoether fraction. The elution fraction was collected and solvent was evaporated to finally obtain 15 g of methyl glucoside.glyceryl stearyl monoether.

Test Example 3

The polyol glyceryl ethers obtained in Synthetic Examples 4–9 of the present invention and the compound obtained in Comparative Example 2 were tested in terms of properties at room temperature and dispersibility in water in the same way as that of Test Example 1. The results are shown in Table 3.

TABLE 3

| Tested Compounds | Property (room temp.) | Dispersibility in water |
|---|---|---|
| Present invention | | |
| Methyl glucoside.glyceryl isostearyl monoether (Syn. Ex. 4) | Liquid crystal | Uniform dispersion |
| Ethyl glucoside.glyceryl isostearyl monoether (Syn. Ex. 5) | Liquid crystal | Uniform dispersion |
| Methyl glucoside.glyceryl 2-heptyl undecyl monoether (Syn. Ex. 6) | Liquid crystal | Uniform dispersion |
| Methyl maltoside.glyceryl 2-octyldodecyl monoether (Syn. Ex. 7) | Liquid crystal | Uniform dispersion |
| Maltitol.glyceryl 2-decyl tetradecyl monoether (Syn. Ex. 8) | Liquid crystal | Uniform dispersion |
| 2,3-Dihydroxypropyl.glyceryl isostearyl monoether (Syn. Ex. 9) | Liquid crystal | Uniform dispersion |
| Comparative compound Methyl glucoside.glyceryl stearyl monoether (Comp. Ex. 2) | Solid | Solid/liquid separation |

Test Example 4

The compounds obtained in Synthetic Examples 4–9, the compound obtained in Comparative Example 2 and conventionally known compounds were used to prepare hair rinse compositions shown in Table 4 in the same way as that of Test Example 2, and their rinsing performance was investigated. The results are also shown in Table 4.

TABLE 4

| Component (wt. %) | Present examples | | | | | |
|---|---|---|---|---|---|---|
| | 4 | 5 | 6 | 7 | 8 | 9 |
| Methyl glucoside.glyceryl isostearyl monoether (Syn. Ex. 4) | 3.0 | — | — | — | — | — |
| Ethyl glucoside.glyceryl isostearyl monoether (Syn. Ex. 5) | — | 3.0 | — | — | — | — |
| Methyl glucoside.glyceryl 2-heptyl undecyl monoether (Syn. Ex. 6) | — | — | 3.0 | — | — | — |
| Methyl maltoside.glyceryl 2-octyldodecyl monoether (Syn. Ex. 7) | — | — | — | 3.0 | — | — |
| Maltitol.glyceryl 2-decyl tetra decyl monoether (Syn. Ex. 8) | — | — | — | — | 3.0 | — |
| 2,3-Dihydroxypropyl glucoside.glyceryl isostearyl monoether (Syn. Ex. 9) | — | — | — | — | — | 3.0 |
| Methyl glucoside.glyceryl stearyl monoether (Comp. Ex. 2) | — | — | — | — | — | — |
| Stearyl glyceryl ether | — | — | — | — | — | — |
| Isostearyl alcohol | — | — | — | — | — | — |
| Stearyl trimethyl ammonium chloride | 2.0 | 2.0 | 2.0 | 2.0 | 2.0 | 2.0 |
| Ion-exchanged water | 95.0 | 95.0 | 95.0 | 95.0 | 95.0 | 95.0 |
| Evaluation Softness | A | A | A | A | A | A |
| Smoothness | A | A | A | A | A | A |
| Reduced greasiness | A | A | A | A | A | A |

| Component (wt. %) | Comparative Examples | | |
|---|---|---|---|
| | 4 | 5 | 6 |
| Methyl glucoside.glyceryl isostearyl monoether (Syn. Ex. 4) | — | — | — |
| Ethyl glucoside.glyceryl isostearyl monoether (Syn. Ex. 5) | — | — | — |
| Methyl glucoside.glyceryl 2-heptyl undecyl monoether (Syn. Ex. 6) | — | — | — |
| Methyl maltoside.glyceryl 2-octyldodecyl monoether (Syn. Ex. 7) | — | — | — |
| Maltitol.glyceryl 2-decyl tetra decyl monoether (Syn. Ex. 8) | — | — | — |
| 2,3-Dihydroxypropyl glucoside.glyceryl isostearyl monoether (Syn. Ex. 9) | — | — | — |
| Methyl glucoside.glyceryl stearyl monoether (Comp. Ex. 2) | 3.0 | — | — |
| Stearyl glyceryl ether | — | 3.0 | — |
| Isostearyl alcohol | — | — | 3.0 |
| Stearyl trimethyl ammonium chloride | 2.0 | 2.0 | 2.0 |
| Ion-exchanged water | 95.0 | 95.0 | 95.0 |
| Evaluation Softness | B | C | C |
| Smoothness | C | B | B |
| Reduced greasiness | B | C | D |

Synthetic Example 10

83 g of diglycerol, 50 g of dimethyl sulfoxide and 0.8 g of sodium hydroxide were placed in a 300 ml flask and heated at 110° C. to form a solution, through which dried nitrogen gas was passed for removing the humidity from the reaction system by expelling about 10 g of water and dimetyl sulfoxide. 33 g of isostearyl glycidyl ether was added dropwise thereto over 1 hour, and reaction was allowed to proceed at 110° C. for 4 hours under agitation.

After the termination of the reaction, 1.2 g of acetic acid was added to the reaction mixture to neutralize the catalyst. Dimethyl sulfoxide was distilled off under reduced pressure at 80° C. The residue was mixed with 500 ml of water and 500 ml of ethyl acetate for ethyl acetate extraction. From the ethyl acetate-soluble fraction, solvent was evaporated to obtain 51 g of a primary purified product, which is a pale yellow diglycerol.isostearyl glycidyl ether adduct.

This primary purified product was further purified by silica gel column chromatography (acetone:hexane=2:1) to elute a target diglycerol-glyceryl isostearyl monoether fraction. The elution fraction was collected and solvent was evaporated to finally obtain 16 g of diglycerol.glyceryl isostearyl monoether.

Hydroxyl value: 451 (Calculated: 456)

NMR (CDCl$_3$): δ (ppm) 3.95~3.85(3H, m, —OCH$_2$—CHOH—CH$_2$O—), 3.67~3.45(14H, m, —OCH$_2$—), 1.30~1.59(29H, b, —CH$_2$—, —CH—), 0.88(6H, m, —CH$_3$)

IR (liquid film) cm$^{-1}$: $\nu_{O-H}$(—OH) 3200~3400; $\nu_{C-H}$ (extension)(—CH—, —CH$_2$—, —CH$_3$) 2850, 2920; $\nu_{C-H}$ (deformation)(—CH—, —CH$_2$—, —CH$_3$) 1375, 1460; $\nu_{C-O}$ (—C—O—) 1110, 1035, 1010

Synthetic Example 11

157 g of tetraglycerol, 100 g of N-methyl pyrrolidone and 1 g of potassium hydroxide were placed in a 300 ml flask and heated at 100° C. to form a solution, through which dried nitrogen gas was passed for removing the humidity from the reaction system by expelling about 10 g of water and N-methyl pyrrolidone. 33 g of isostearyl glycidyl ether was added dropwise thereto over 5 hours, and reaction was allowed to proceed at 110° C. for 4 hours under agitation.

After the termination of the reaction, 1.5 g of acetic acid was added to the reaction mixture to neutralize the catalyst. N-methyl pyrrolidone was distilled off under reduced pressure at 80° C. The residue was mixed with 500 ml of methylethyl ketone and 1000 ml of water for ethyl acetate extraction. From the ethyl acetate-soluble fraction, ethyl acetate was evaporated to obtain 61 g of a primary purified product, tetraglycerol.isostearyl glycidyl ether adduct.

This primary purified product was further purified by silica gel column chromatography (chloroform:methanol=4:1) to elute a target tetraglycerol.glyceryl isostearyl monoether fraction. The elution fraction was collected and solvent was evaporated to finally obtain 19 g of tetraglycerol.glyceryl isostearyl monoether.

Hydroxyl value: 532 (Calculated: 526)

NMR(CDCl$_3$: δ (ppm) 3.95~3.75(5H, m, —OCH$_2$—CHOH—CH$_2$O—), 3.67~3.45(22H, m, —OCH$_2$—), 1.30~1.59(29H, b, —CH$_2$—, —CH—), 0.88(6H, m, —CH$_3$)

IR (liquid film) cm$^{-1}$: $\nu_{O-H}$(—OH) 3200~3400; $\nu_{C-H}$ (extension)(—CH—, —CH$_2$—, —CH$_3$) 2835~2910; $\nu_{C-H}$ (deformation)(—CH—, —CH$_2$—, —CH$_3$) 1370, 1445; $\nu_{C-O}$ (—C—O—) 1030~1110

Synthetic Example 12

83 g of diglycerol, 50 g of dimethyl sulfoxide and 0.8 g of sodium hydroxide were placed in a 300 ml flask and heated at 120° C. to form a solution, through which dried nitrogen gas was passed for removing the humidity from the reaction system by expelling about 10 g of water and dimethyl sulfoxide. 35 g of 2-octyldodecyl glycidyl ether was added dropwise thereto over 2 hours, and reaction was allowed to proceed at 120° C. for 6 hours under agitation.

After the termination of the reaction, 1.2 g of acetic acid was added to the reaction mixture to neutralize the catalyst. Dimethyl sulfoxide was completely distilled off under reduced pressure at 80° C. The residue was mixed with 500 g of water and then extracted with 1000 ml of methylethyl ketone (500 ml×2). The obtained methylethyl ketone layer was dried over Glauber's salt, followed by filtration and distillation of the solvent to obtain 53 g of a primary purified diglycerol.2-octyldodecyl glycidyl ether adduct.

This primary purified product was further purified by silica gel column chromatography (chloroform:methanol=5:1) to elute a target diglycerol.glyceryl 2-octyldodecyl monoether fraction. The elution fraction was collected and solvent was evaporated to finally obtain 29 g of diglycerol.glyceryl 2-octyldodecyl monoether.

Hydroxyl value: 527 (Calculated: 529)

NMR(CDCl$_3$): δ (ppm) 3.95~3.78(3H, m, —OCH$_2$—CHOH—CH$_2$O—), 3.65~3.45(14H, m, —OCH$_2$—), 1.30~1.59(33H, b, —CH$_2$—, —CH—), 0.87(6H, m, —CH$_3$)

IR (liquid film) cm$^{-1}$: $\nu_{O\text{-}H}$(—OH) 3200~3400; $\nu_{C\text{-}H}$ (extension)(—CH—, —CH$_2$—, —CH$_3$) 2860, 2930; $\nu_{C\text{-}H}$ (deformation)(—CH—, —CH$_2$—, —CH$_3$) 1380, 1440; $\nu_{C\text{-}O}$(—C—O—) 1030~1120

Comparative Example 3

The procedure of Synthetic Example 1 was followed using 33 g of stearyl glycidyl ether instead of isostearyl glycidyl ether, to prepare diglycerol-stearyl glycidyl ether adduct. The reaction mixture was purified by silica gel column chromatography to obtain 15 g of diglycerol-glyceryl stearyl monoether.

Test Example 5

The compounds obtained in Synthetic Examples 10–12 of the present invention and compound obtained in Comparative Example 3 were tested in terms of properties at room temperature and dispersibility in water in the same way as that of Test Example 1. The results are shown in Table 5.

TABLE 5

| Tested Compounds | Property (room temp.) | Dispersibility in water |
|---|---|---|
| Present invention | | |
| Diglycerol.glyceryl isostearyl monoether (Syn. Ex. 10) | Liquid crystal | Uniform dispersion |
| Tetraglycerol.glyceryl isostearyl monoether (Syn. Ex. 11) | Liquid crystal | Uniform dispersion |
| Diglycerol.glyceryl 2-octyldodecyl monoether (Syn. Ex. 12) | Liquid crystal | Uniform dispersion |
| Comparative compound Diglycerol.glyceryl stearyl monoether (Comp. Ex. 3) | Solid | Solid/liquid separation |

Test Example 6

The compounds obtained in Synthetic Examples 10–12, the compound obtained in Comparative Example 3 and conventionally known compounds were used to prepare hair rinse compositions shown in Table 6 in the same way as that of Test Example 2 and their rinsing performance was investigated. The results are also shown in Table 6.

TABLE 6

| | Present examples | | | Comparative examples | | |
|---|---|---|---|---|---|---|
| Component (wt. %) | 10 | 11 | 12 | 7 | 8 | 9 |
| Diglycerol.glyceryl isostearyl monoether (Syn. Ex. 10) | 3.0 | — | — | — | — | — |
| Tetraglycerol.glyceryl isostearyl monoether (Syn. Ex. 11) | — | 3.0 | — | — | — | — |
| Diglycerol.glyceryl 2-octyldodecyl monoether (Syn. Ex. 12) | — | — | 3.0 | — | — | — |
| Diglycerol.glyceryl stearyl monoether (Comp. Ex. 3) | — | — | — | 3.0 | — | — |
| Stearyl monoglyceryl ether | — | — | — | — | 3.0 | — |
| Isostearyl monoglyceryl ether | — | — | — | — | — | 3.0 |
| Stearyl trimethyl ammonium chloride | 2.0 | 2.0 | 2.0 | 2.0 | 2.0 | 2.0 |
| Ion-exchanged water | 95.0 | 95.0 | 95.0 | 95.0 | 95.0 | 95.0 |
| Evaluation Softness | A | A | A | C | C | B |
| Smoothness | A | A | A | C | B | B |
| Reduced greasiness | A | A | A | B | C | D |

Synthetic Example 13

80 g of trimethylol propane, 100 g of dimethyl sulfoxide and 1 g of sodium hydroxide were placed in a 300 ml flask and heated at 105° C. to form a solution, through which dried nitrogen gas was passed for removing the humidity from the reaction system by expelling about 10 g of water and dimethyl sulfoxide. 39 g of glycidyl isostearyl ether was added dropwise thereto over 1 hour, and reaction was allowed to proceed at 105° C. for 4 hours under agitation.

After the termination of the reaction, 1.5 g of acetic acid was added to the reaction mixture to neutralize the catalyst. Dimethyl sulfoxide was distilled off under reduced pressure at 80° C. The residue was mixed with 500 g of water and then extracted with 500 ml of ethyl acetate (250 ml×2) for ethyl acetate extraction. The ethyl acetate was evaporated from the ethyl acetate soluble fraction under reduced pressure, to obtain 62 g of a primary purified trimethylol propane-glyceryl isostearyl monoether.

This primary purified product was further purified by silica gel column chromatography (acetone:hexane=5:1) to elute a target trimethylol propane-glyceryl isostearyl monoether fraction. The elution fraction was collected and solvent was evaporated to finally obtain 26 g of trimethylol propane.glyceryl isostearyl monoether, which was a colorless transparent liquid (yield: 46%).

Figure 3:
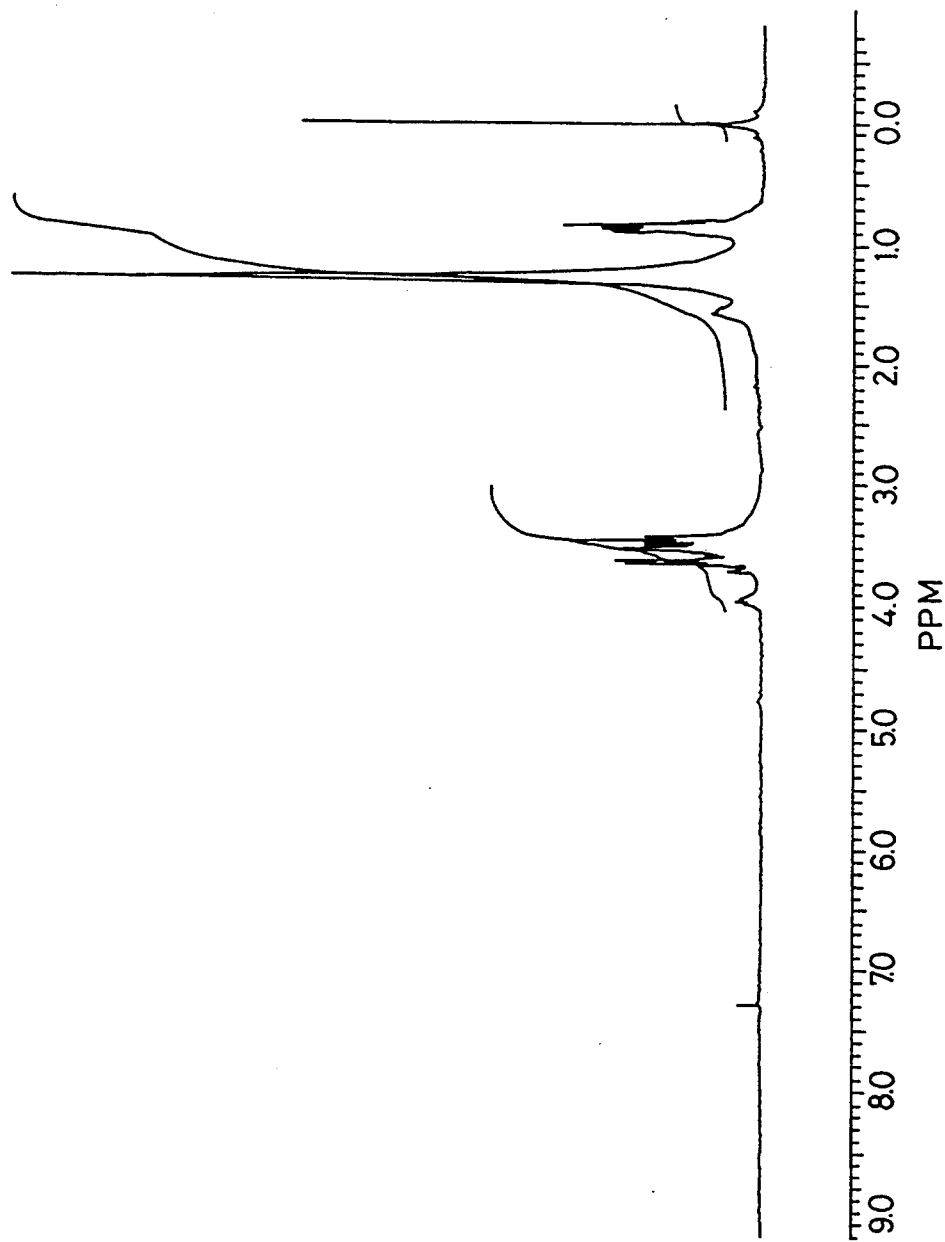
FIG. 3 is a chart showing the NMR spectrum of a trimethylol propane.glyceryl isostearyl monoether obtained in Synthetic Example 13.
Figure 4:
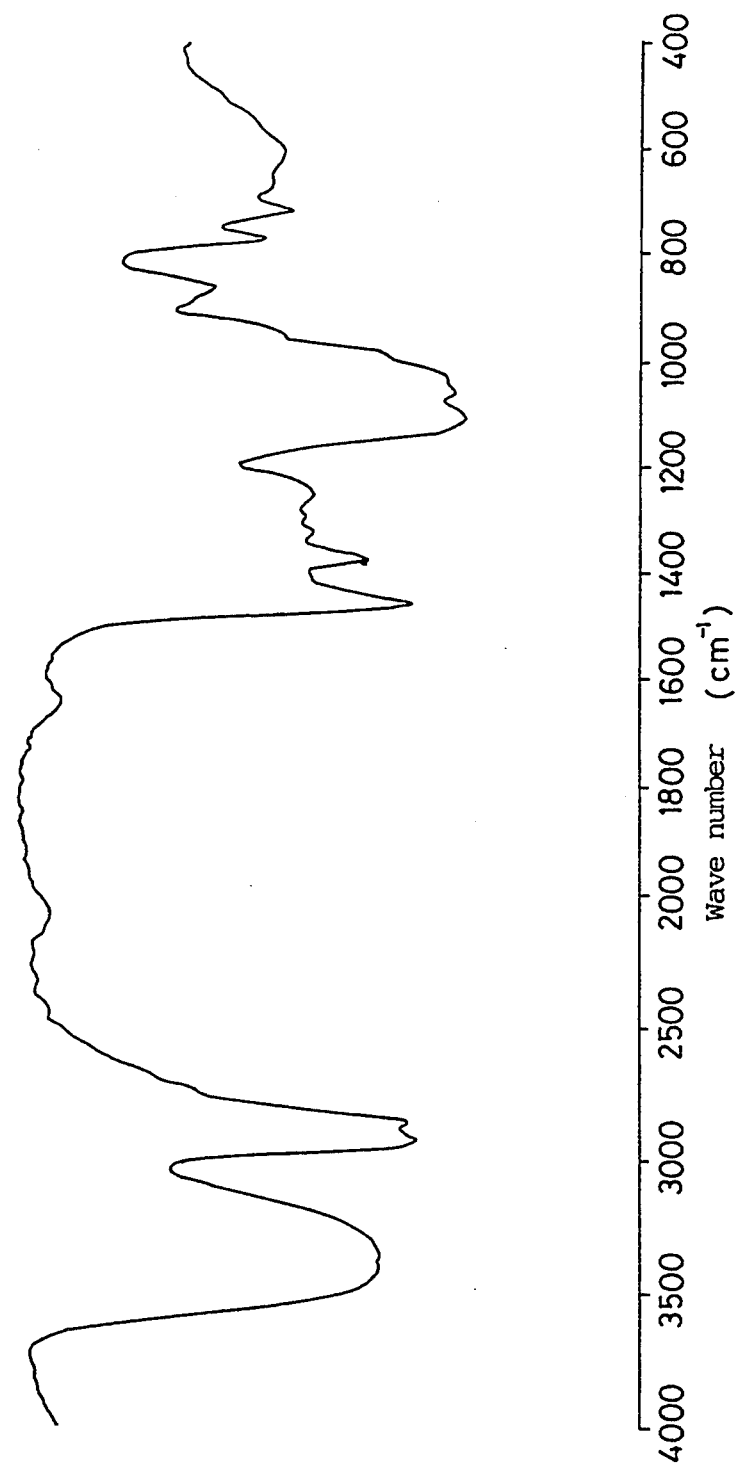
FIG. 4 is a chart showing the IR spectrum of the trimethylol propane.glyceryl isostearyl monoether obtained in Synthetic Example 13.

The NMR spectrum and the IR spectrum of the obtained compound are shown in FIG. 3 and FIG. 4, respectively.

NMR(CDCl$_3$): δ (ppm) 3.94(1H, m, —OCH$_2$—CHOH—CH$_2$O—), 3.41~3.70(12H, m, —CH$_2$OH, —OCH$_2$—), 1.27~1.58(31H, b, —CH$_2$—, —CH—), 0.83(9H, m, —CH$_3$)

IR (liquid film) cm$^{-1}$: $\nu_{O\text{-}H}$(—OH) 3200~3400; $\nu_{C\text{-}H}$ (extension)(—CH—, —CH$_2$—, —CH$_3$) 2850, 2930;

$v_{C-H}$ (deformation)(—CH—, —CH$_2$—, —CH$_3$) 1380, 1440; $v_{C-O}$(—C—O—) 1110, 1060

Synthetic Example 14

72 g of trimethylol ethane, 50 g of N-methyl pyrrolidone and 1 g of sodium hydroxide were placed in a 300 ml flask and heated at 120° C. to form a solution, through which dried nitrogen gas was passed for removing the humidity from the reaction system by expelling about 10 g of water and N-methyl pyrrolidone. 39 g of glycidyl isostearyl ether was added droppwise thereto over 2 hours, and reaction was allowed to proceed at 120° C. for 4 hours under agitation.

After the termination of the reaction, 1.5 g of acetic acid was added to the reaction mixture to neutralize the catalyst. N-methyl pyrrolidone was distilled off under reduced pressure at 80° C. Unreacted trimethylol ethane was evaporated with Smith's evaporator to obtain 55 g of a primary purified trimethylol ethane.glyceryl isostearyl ether.

This primary purified product was further purified by silica gel column chromatography (hexane:acetone=4:1) to elute a trimethylol ethane.glyceryl isostearyl monoether fraction. The elution fraction was collected and solvent was evaporated to finally obtain 20 g of the target trimethylol ethane.glyceryl isostearyl monoether (yield: 39%).

NMR(CDCl$_3$): δ (ppm) 3.95(1H, m, —OCH$_2$—CHOH—CH$_2$O—), 3.40~3.69(12H, m, —CH$_2$OH, —OCH$_2$—), 1.28~1.57(29H, b, —CH$_2$—, —CH—), 0.89(9H, m, —CH$_3$)

IR (liquid film) cm$^{-1}$: $v_{O-H}$(—OH) 3200~3400; $v_{C-H}$ (extension)(—CH—, —CH$_2$—, —CH$_3$) 2840~2910; $v_{C-H}$ (deformation)(—CH—, —CH$_2$—, —CH$_3$) 1370, 1450; $v_{C-O}$(—C—O—) 1110, 1070

Synthetic Example 15

80 g of trimethylol propane, 50 g of dimethyl sulfoxide and 0.8 g of sodium hydroxide were placed in a 300 ml flask and heated at 120° C. to form a solution, through which dried nitrogen gas was passed for removing the humidity from the reaction system by expelling about 10 g of water and dimethyl sulfoxide. 40 g of glycidyl octyldodecyl ether was added dropwise thereto over 2 hours, and reaction was allowed to proceed at 120° C. for 6 hours under agitation.

After the termination of the reaction, 1.2 g of acetic acid was added to the reaction mixture to neutralize the catalyst. Dimethyl sulfoxide was distilled off under reduced pressure at 80° C. The residue was mixed with 500 g of water and then extracted with 1000 ml of methylethyl ketone (500 ml×2). The obtained methylethyl ketone layer was dried over Glauber's salt, followed by filtration and distillation of the solvent to obtain 53 g of a primary purified trimethylol propane.glyceryl octyldodecyl ether adduct.

This primary purified product was further purified by silica gel column chromatography (hexane:acetone=5:1) to elute a target trimethylol propane.glyceryl octyldodecyl monoether fraction. The elution fraction was collected and solvent was evaporated to finally obtain 29 g of a trimethylol propane.glyceryl octyldodecyl monoether (yield: 46%).

NMR(CDCl$_3$): δ (ppm) 3.97(1H, m, —OCH$_2$—CHOH—CH$_2$O—), 3.41~3.70(12H, m, —CH$_2$OH, —OCH$_2$—), 1.24~1.58(35H, b, —CH$_2$—, —CH—), 0.85(9H, m, —CH$_3$)

IR (liquid film) cm$^{-1}$: $v_{O-H}$(—OH) 3200~3400; $v_{C-H}$ (extension)(—CH—, —CH$_2$—, —CH$_3$) 2860, 2930; $v_{C-H}$ (deformation)(—CH—, —CH$_2$—, —CH$_3$) 1380, 1440; $v_{C-O}$(—C—O—) 1120, 1060

Comparative Example 4

70 g of trimethylol propane, 200 g of dimethyl sulfoxide and 1 g of sodium hydroxide were placed in a 500 ml flask and heated at 100° C. to form a solution, through which dried nitrogen gas was passed for removing the humidity from the reaction system by expelling about 20 g of water and dimethyl sulfoxide. 33 g of glycidyl stearyl ether was added dropwise thereto over 2 hours, and reaction was allowed to proceed at 110° C. for 5 hours under agitation.

After the termination of the reaction, 1.5 g of acetic acid was added to the reaction mixture to neutralize the catalyst. Dimethyl sulfoxide was distilled off under reduced pressure at 80° C. The residue was added with 500 g of acetone, and unreacted trimethylol propane which was precipitated was filtered out. From the obtained filtrate, acetone was evaporated under reduced pressure to obtain 45 g of a primary purified product, trimethylol propane-glyceryl stearyl ether.

This primary purified product was further purified by silica gel column chromatography (hexane:acetone=2:1) to elute a target trimethylol propane.glyceryl stearyl monoether fraction. The elution fraction was collected and solvent was evaporated to finally obtain 22 g of a trimethylol propane-glyceryl stearyl monoether (yield: 47%).

It was confirmed by NMR and IR spectrum analyses that the obtained compound was trimethylol propane.glyceryl stearyl monoether.

Test Example 7

The trimethylol alkane derivatives obtained in Synthetic Examples 13–15 of the present invention, the compound obtained in Comparative Example 4 and conventionally known compounds were tested in terms of properties at room temperature and dispersibility in water in the same way as that of Test Example 1. The results are shown in Table 7.

TABLE 7

| Tested Compounds | Property (room temp.) | Dispersibility in water |
| --- | --- | --- |
| Present invention | | |
| Trimethylol propane .glyceryl isostearyl monoether (Syn. Ex. 13) | Liquid | Uniform dispersion |
| Trimethylol ethane.glyceryl isostearyl monoether (Syn. Ex. 14) | Liquid | Uniform dispersion |
| Comparative compounds | | |
| Trimethylol propane.glyceryl stearyl monoether (Comp. Ex. 4) | Solid | Solid/liquid separation |
| Stearyl monoglyceryl ether | Solid | Solid/liquid separation |
| Isostearyl alcohol | Liquid | Liquid/liquid separation |

Test Example 8

The compounds obtained in Synthetic Examples 13–15 and Comparative Example 4 and conventionally known compounds were used to prepare hair rinse compositions as shown in Table 8 in the same way as that of Test Example 2, and their rinsing performance was investigated. The results are also shown in Table 8.

A: Excellent
B: Good
C: Moderate
D: Inferior

TABLE 8

| Component (wt. %) | Present examples | | | Comparative examples | | |
|---|---|---|---|---|---|---|
| | 13 | 14 | 15 | 10 | 11 | 12 |
| Trimethylol propane. glyceryl isostearyl monoether (Syn. Ex. 13) | 3.0 | — | — | — | — | — |
| Trimethylol ethane. glyceryl isostearyl monoether (Syn. Ex. 14) | — | 3.0 | — | — | — | — |
| Trimethylol propane. glyceryl stearyl monoether (Comp. Ex. 4) | — | — | — | 3.0 | — | — |
| Stearyl glyceryl ether | — | — | — | — | 3.0 | — |
| Isostearyl alcohol | — | — | — | — | — | 3.0 |
| Stearyl trimethyl ammonium chloride | 2.0 | 2.0 | 2.0 | 2.0 | 2.0 | 2.0 |
| Ion-exchanged water | 95.0 | 95.0 | 95.0 | 95.0 | 95.0 | 95.0 |
| Evaluation Softness | A | A | A | B | C | C |
| Smoothness | A | A | A | C | B | B |
| Reduced greasiness | A | A | A | B | C | D |

Synthetic Example 16

29.9 g (0.1 mol) of methyl isostearate, 68 g (0.5 mol) of pentaerythritol, 1.9 g of 28% sodium methylate/methanol solution and 450 ml of dimethyl formamide were placed in a 1-liter reaction vessel provided with an evaporation cooling tube with a thermometer, a stirrer and a pressure reducing apparatus. Reaction was allowed to proceed at 100° C. for 2.5 hours under a reduced pressure of 100–120 mmHg. During this reaction, about 100 ml of dimethyl formamide was expelled. The reaction mixture was cooled, then mixed with about 400 ml of water for separation in layers. Ether was added to the lower layer for extraction, and the ether layer was added to the upper layer, which was firstly separated, followed by washing with water three times. The ether was evaporated under reduced pressure to obtain a primary purified pentaerythritol monoisostearate of 77% purity (yield: 70%).

This primary purified product was further purified by silica gel column chromatography (ethyl acetate/ethanol) until a single spot was obtained in a thin layer chromatograpy to obtain 21 g of pentaerythritol monosisostearate of 94% purity (yield: 50%).

IR (liquid film) cm$^{-1}$: 3450(O—H), 2840~2950(C—H), 1720(C=O), 1640(C—H), 1040(C—O)

$^1$H-NMR(CDCl$_3$) δ ppm:

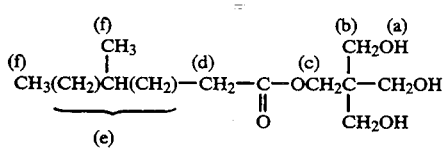

4.1[(c),2H], 3.6[(b),6H], 3.3[(a),3H], 2.4[(d),2H], 1.1–1.7[(e), 27H], 0.9[(f),6H]

Synthetic Example 17

(1) 160 g (0.88 mol) of glucose, 956 g (8.8 mol) of 3-chloro-1,2-propanediol and 40 g of DOWEX (trademark) 50WX8 (type H, 50–100 mesh), as an acid catalyst, were placed in a reaction vessel, and heated at 60° C. under agitation, followed by reaction for 16 hours. After the termination of the reaction, unreacted 3-chloro-,1,2-propanediol was filtered off under reduced pressure with a glass filter. The obtained residue was washed three times with 500 g of acetone, and dried under reduced pressure to obtain 79 g of 3-chloro-2-hydroxy-1-O-glucosyl propane (yield: 33%).

(2) 83 g (0.3 mol) of 3-chloro-2-hydroxy-1-O-glucosyl propane obtained in the reaction (1), 47 g (0.15 mol) of sodium isostearate, 1 g of tetrabutyl ammonium bromide and 200 ml of dimethyl formamide were placed in a reaction vessel, and heated at 100° C. under agitation, followed by reaction for 8 hours. After the termination of the reaction, the dimethyl formamide was distilled off under reduced pressure. The residue was mixed with 300 g of water and 600 g of ethyl acetate, and, after vigorous shaking, the residue was allowed to stand to recover an ethyl acetate layer. From this layer, ethyl acetate was distilled off under reduced pressure to obtain a primary purified product.

This primary purified product was further purified by silica gel column chromatography (chloroform:methanol = 10:1) to obtain 14 g of 3-O-isostearoyl-1-O-glucosyl glycerol (separation yield: 26%).

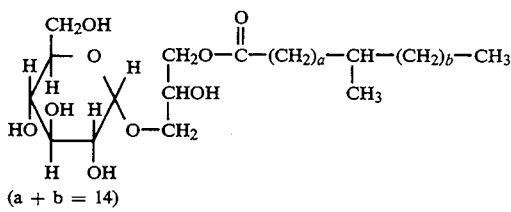

(a + b = 14)

$^1$H-NMR(CDCl$_3$) δ (ppm, TMS standard) 0.79~1.03(t, 6H), 1.11~1.45(broad, 25H), 1.56(broad, 2H), 2.33(broad, 2H), 3.23~4.39(m, 11H), 4.88(broad, 1H)

IR (liquid film) cm$^{-1}$: 3400, 2950~2860, 1740, 1650, 1470, 1390~950 Mass analysis by FAB ionization method: m/z: 521 (M+H)$^+$

Test Example 9

The nonionic amphipathic compounds obtained Synthetic Examples 1,2,4,8 and 16 of the present invention were tested in terms of properties at room temperature (25° C.) and 55° C., and dispersibility in water (concentration: 5% by weight). The results are shown in Table 9.

Evaluation Method

Properties at 25° C. and 55° C. were checked by a polarization plate, a polarization microscope, X-ray diffraction, DSC or the like. The state of an aqueous system was tested in the following manner: 1 g of a test sample was collected in a 30 ml vial, to which ion-exchanged water was added so as to make the sample concentration 5% by weight. The sample vial was heated and agitated repeatedly for a uniform mixture, then observed in a similar manner as properties were checked.

TABLE 9

| Tested Compounds | Property | | State in Aqueous System |
|---|---|---|---|
| | 25° C. | 55° C. | |
| Synthetic Ex. 1 | Lamellar | Lamellar | Formation of lamellar |

TABLE 9-continued

| Tested Compounds | Property 25° C. | Property 55° C. | State in Aqueous System |
|---|---|---|---|
| | liquid crystal | liquid crystal | liquid crystal, uniform dispersion |
| Synthetic Ex. 2 | Lamellar liquid crystal | Lamellar liquid crystal | Formation of lamellar liquid crystal, uniform dispersion |
| Synthetic Ex. 4 | Lamellar liquid crystal | Lamellar liquid crystal | Formation of lamellar liquid crystal, uniform dispersion |
| Synthetic Ex. 8 | Lamellar liquid crystal | Lamellar liquid crystal | Formation of lamellar liquid crystal, uniform dispersion |
| Synthetic Ex. 16 | Lamellar liquid crystal | Lamellar liquid crystal | Formation of lamellar liquid crystal, uniform dispersion |

EXAMPLE 1

Hair rinse compositions shown in Table 10 were prepared, and their rinsing performance was investigated. The results are also shown in Table 10.

Preparation

To 70° C. water were added ingredients which were heated at 70° C. and dissolved in advance, and stirred to mix, followed by cooling down to room temperature while stirring to prepare hair rinse compositions.

Evaluation method 20 g of sample hair (15 cm long) of Japanese women who had never experienced cold perming or bleaching was provided. The hair tress was shampooed with a commercially available shampoo containing an anionic surfactant as a major component, then 2 g of a hair rinse composition shown in Table 10 was uniformly applied to the hair. Rinsing under running water was conducted for 30 seconds, followed by towel-drying. The hair tress in the moistened state was organoleptically evaluated in terms of smoothness, moisture retentivity and reduced greasiness. The evaluation standards are as follows:
A: Excellent
B: Good
C: Moderate
D: Inferior

TABLE 10

| Component (wt. %) | Comparative examples 13 | Comparative examples 14 | Present examples 16 | Present examples 17 |
|---|---|---|---|---|
| (1) Stearyl trimethyl ammonium chloride | 2.0 | 2.0 | 2.0 | 2.0 |
| (2) Cetyl alcohol | 3.0 | 3.0 | 3.0 | 3.0 |
| (3) Pentaerythritol. glyceryl isostearyl monoether (Syn. Ex. 1) | — | — | 3.0 | — |
| Pentgerythritol monoisostearate (Syn. Ex. 16) | — | — | — | 3.0 |
| (4) Propylene glycol | — | 3.0 | 3.0 | 3.0 |
| (5) Water | Balance | Balance | Balance | Balance |
| [Evaluation] Effects to hair — Smoothness | C | C | A | A |
| Moisture-retentivity | C | B | A | A |
| Reduced greasiness | D | C | A | A |

Example 2

| Hair treatment composition: | |
|---|---|
| (1) 2-dodecylhexadecyl trimethyl ammonium chloride | 1.5 (wt. %) |
| (2) Stearyl trimethyl ammonium chloride | 2.0 |
| (3) Dimethyl polysiloxane (500 cs) | 1.0 |
| (4) Cetostearyl alcohol | 3.0 |
| (5) Pentaerythritol.glyceryl isostearyl monoether (Syn. Ex. 1) | 3.0 |
| (6) Liquid paraffin | 3.0 |
| (7) Hydroxyethylcellulose (1% solution, viscosity:8000 cp) | 0.5 |
| (8) Polyoxyethylene oleyl ether (EO = 5) | 0.5 |
| (9) Glycerol | 10.0 |
| (10) Methylparaben | 0.2 |
| (11) Perfume | 0.4 |
| (12) Water | balance |
| Total | 100.0 |

The hair treatment composition exhibited remarkable smoothness, softness and little greasiness, thereby giving a light, moistened and nice feel to users.

EXAMPLE 3

| Hair cream composition: | |
|---|---|
| (1) Di(2-hexadecyl)dimethyl ammonium chloride | 2.0 (wt. %) |
| (2) Cetyltrimethyl ammonium chloride | 1.0 |
| (3) Methy glucoside.glyceryl isostearyl monoether (Syn. Ex. 4) | 1.0 |
| (4) Cetyl alcohol | 5.0 |
| (5) Dipropylene glycol | 6.0 |
| (6) Glycerol | 10.0 |
| (7) Liquid paraffin | 3.0 |
| (8) Perfume | 0.4 |
| (9) water | balance |
| Total | 100.0 |

The hair cream composition exhibited remarkable smoothness, softness and little greasiness, thereby giving nice feel to users.

EXAMPLE 4

| Conditioning mousse composition: | |
|---|---|
| (1) Di(2-hexadecyl)dimethyl ammonium chloride | 0.5 (wt. %) |
| (2) Methyl phenyl porysiloxane (300 cs) | 1.0 |
| (3) Isotridecyl myristate | 1.0 |
| (4) 3-Methyl-1,3-butanediol | 1.0 |
| (5) Glycerol | 2.5 |
| (6) Liquid paraffin | 2.5 |
| (7) Pentaerythritol monoisostearate (Syn. Ex. 16) | 0.2 |
| (8) 95% ethyl alcohol | 5.0 |
| (9) Methyl paraben | 0.1 |
| (10) Perfume | 0.1 |
| (11) LPG (4.0 Kg/cm$^2$G, 20° C.) | 10.0 |
| (12) Purified water | balance |
| Total | 100.0 |

The conditioning mousse composition gave nice feel to users.

EXAMPLE 5

| Cream composition: | |
|---|---|
| Oil Ingredients: | |
| Cetanol | 2.0 (wt. %) |
| Stearic acid | 3.0 |
| Trimethylol isoheptadecane | 3.0 |
| Maltitol.glyceryl 2-decyltetradecyl monoether (Syn. Ex. 4) | 2.0 |
| Lipids (isostearic acid cholesteryl ester) | 8.0 |
| Monolauryl glycerol | 2.0 |
| Polyoxyethylene (20) sorbitan monolaurate | 2.0 |
| Aqueous Ingredients: | |
| Dipropylene glycol | 10.0 |
| 1,3-butylene glycol | 5.0 |
| Ethylparaben | 0.1 |
| Methylparaben | 0.2 |
| Perfume | 0.1 |
| Purified water | balance |
| Total | 100.0 |

The cream composition gave nice feel to users and had an excellent moisturing effect.

EXAMPLE 6

| Milk composition: (milky lotion) | |
|---|---|
| Oil Ingredients: | |
| Cetanol | 0.5 (wt %) |
| Stearic Acid | 2.0 |
| Vaseline | 1.0 |
| 3-O-isostearoyl-1-O-glucosyl glycerol (Syn. Ex. 17) | 3.0 |
| Polyoxyethylene(10)monooleate | 2.0 |
| Dimethyl polysiloxane(500 cs) | 1.0 |
| Aqueous Ingredients: | |
| Dipropylene glycol | 6.0 |
| 1,3-butylene glycol | 3.0 |
| Methylparaben | 0.2 |
| Perfume | 0.1 |
| Purified water | balance |
| Total | 100.0 |

The milk composition gave nice feel to users and had an excellent moisturring effect.

What is claimed is:

1. A polyol glyceryl ether represented by the formula (2')

wherein G, A, B, x and y are as follows:

G is a trimethylolalkane residual group represented by formula (3a) or a pentaerythritol residual group represented by formula (3b):

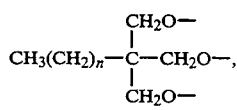

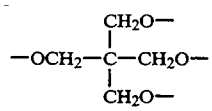

wherein n is an integer of 0–4, or a residual group obtained by removing hydrogen atoms from all the hydroxy groups of a polyol having four or more hydroxyl groups excepting sucrose, fructofuranose, fructopyranose, polyglycerol and glucopyranose;

each A is independently an alkylene group having 2–4 carbon atoms;

each B is independently a hydrogen atom or a —CH$_2$CH(OH)CH$_2$OR$^{4'}$ and/or

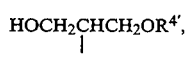

wherein R$^{4'}$ is a branched alkyl group having 10–36 carbon atoms, provided that at least one of said B groups is —CH$_2$CH(OH)CH$_2$OR$^{4'}$ and/or

x is a number of 0–10 obtained by dividing, by y, the total mol number of added alkylene oxide to the hydroxyl groups of the trimethylolalkane or polyol; and y is the number of hydroxyl groups of the trimethylolalkane or polyol, wherein said polyol glyceryl ether has a lamellar liquid crystal structure at 25° C. and at 50° C. or higher.

2. The polyol glyceryl ether of claim 1, wherein R$^{4'}$ in said formula (2') is represented by formula (7):

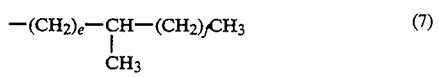

wherein e and f are integers of 0–33, respectively, and the sum of e and f is 13—33; or is represented by formula (8):

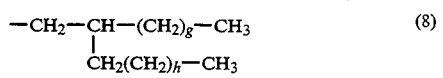

wherein g and h are integers of 0–31, respectively, and the sum of g and h is 11–31.

3. The polyol glyceryl ether of claim 1, wherein G in said formula (2') is a residual group obtained by removing hydrogen atoms from all the hydroxy groups of at least one polyol selected from the group consisting of pentaerythritol, sorbitol, manitol, maltitol and glycosides or represented by the following formulas:

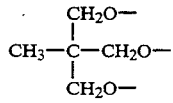

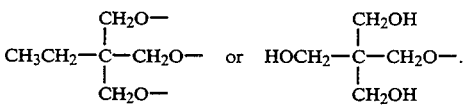

4. The polyol glyceryl ether of claim 1, wherein R$^{4'}$ in said formula (2') is represented by formula (7):

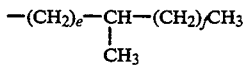 (7)

wherein e and f are integers of 0–33, respectively, and the sum of e and f is 13–33; or represented by formula (8):

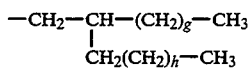 (8)

wherein g and h are integers of 0–31, respectively, and the sum of g and h is 11–31; and wherein G in said formula (2') is a residual group obtained by removing hydrogen atoms from all the hydroxy groups of at least one polyol selected from the group consisting of pentaerythritol, sorbitol, manitol, maltitol and glycosides or represented by the following formulas:

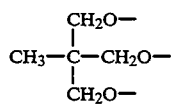

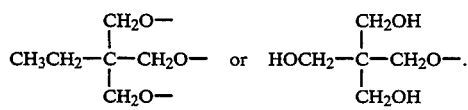

5. The polyol glyceryl ether of claim 1, wherein $R^{4'}$ in said formula (2') is represented by formula (7):

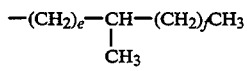 (7)

wherein e and f are integers of 0–33, respectively, and the sum of e and f is 13–33; and G is a residual group obtained by removing hydrogen atoms from all the hydroxyl groups of at least one polyol selected from the group consisting of pentaerythritol, sorbitol, manitol, maltitol and glycosides.

6. The glyceryl ether of claim 1, wherein $R^{4'}$ in said formula (2') is represented by formula (7):

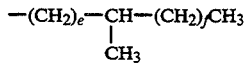 (7)

wherein e and f are integers of 0–33, respectively, and the sum of e and f is 13–33; and G is pentaerythritol.

7. A polyol glyceryl ether according to claim 1, wherein G in said formula (2') is a residual group obtained by removing hydrogen atoms from all the hydroxyl groups of at least one polyol selected from the group consisting of pentaerythritol, sorbitol, mannitol, maltitol and glycosides.

8. A polyol glyceryl ether according to claim 1, wherein G in said formula (2') is a residual group obtained by removing hydrogen atoms from all the hydroxyl groups of glycosides having alkyl, alkenyl or alkyl ether groups which have 1–22 carbon atoms and may have a straight or branched chain and which may be substituted by hydroxyl.

9. A polyol glyceryl ether according to claim 1, wherein G in said formula (2') is a residual group obtained by removing hydrogen atoms from all the hydroxyl groups of glycosides having a sugar condensation degree of 1–2.

10. A polyol glyceryl ether according to claim 1, wherein G in said formula (2') is a residual group obtained by removing hydrogen atoms from all the hydroxyl groups of methyl glucoside, ethyl glucoside, methyl maltoside, ethyl maltoside or 2,3-dihydroxypropyl glucoside.

11. A polyol glyceryl ether according to claim 1, wherein G in said formula (2') is represented by following formulas:

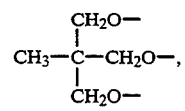

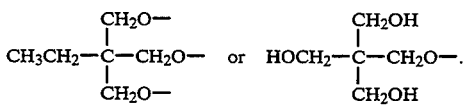

12. A polyol glyceryl ether according to claim 1, wherein $R^{4'}$ in said formula (2') is represented by formula (7):

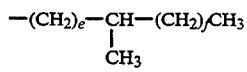 (7)

wherein e and f are integers of 0–33, respectively, and the sum of e and f is 13–33.

13. A polyol glyceryl ether according to claim 1, wherein $R^{4'}$ in said formula (2') is represented by formula (8):

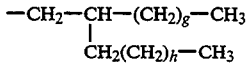 (8)

wherein G and h are integers of 0–31, respectively, and the sum of g and h is 11–31.

14. A method of preparing a polyol glyceryl ether represented by formula (2')

 (2')

wherein G, A, B, x and y have the following meanings:
G is a trimethylolalkane residual group represented by formula (3a) or a pentaerythritol residual group represented by formula (3b):

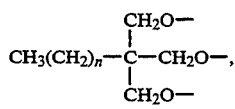 (3a)

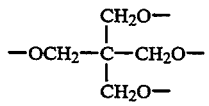 (3b)

wherein n is an integer of 0–4,
or a residual group obtained by removing hydrogen atoms from all the hydroxyl groups of a polyol having four or more hydroxyl groups, excepting sucrose, fructofuranose, fructopyranose and glucopyranose;

each A is independently an alkylene group having 2–4 carbon atoms;

each B is independently a hydrogen atom or —CH$_2$CH(OH)CH$_2$OR$^{4'}$ and/or $$HOCH_2\underset{|}{C}HCH_2OR^{4'},$$

wherein R$^{4'}$ is a branched alkyl group having 16–36 carbon atoms, provided that at least one of said B groups is —CH$_2$CH(OH)CH$_2$OR$^{4'}$ and/or $$HOCH_2\underset{|}{C}HCH_2OR^{4'};$$

x is a number of 0–10 obtained by dividing, by y, the total mol number of added alkylene oxide to the hydroxyl groups of the trimethylolalkane or polyol;

y is the number of hydroxyl groups of the trimethylolalkane or polyol;

said method comprising reacting a trimethylolalkane, a polyol having four or more hydroxyl groups, excepting sucrose, fructofuranose, fructopyranose, polyglycerol and glucopyranose, or a compound thereof represented by formula (9):

$$G-\!\!+\!\!(AO)_{\overline{x}}H)_y \qquad (9)$$

wherein G, A, x and y have the aforementioned meanings, and a glycidyl branched alkyl ether represented by formula (10):

$$\underset{O}{CH_2\!\!\!\diagdown\!\!\!\!\diagup\!\!\!CHCH_2OR^{4'}} \qquad (10)$$

wherein R$^{4'}$ is a branched alkyl group having 16–36 carbon atoms,
in the presence of a basic catalyst.

* * * * *